United States Patent
Franco Rodriguez et al.

(10) Patent No.: US 10,809,212 B2
(45) Date of Patent: Oct. 20, 2020

(54) METHOD FOR THE ANALYSIS OF GLYCOSAMINOGLYCANS, AND THEIR DERIVATIVES AND SALTS BY NUCLEAR MAGNETIC RESONANCE

(71) Applicant: LABORATORIOS FARMACÉUTICOS ROVI, S.A., Madrid (ES)

(72) Inventors: Guillermo Franco Rodriguez, Madrid (ES); Ibon Gutierro Aduriz, Madrid (ES)

(73) Assignee: LABORATORIOS FARMACÉUTICOS ROVI, S.A., Madrid (ES)

( * ) Notice: Subject to any disclaimer, the term of this patent is extended or adjusted under 35 U.S.C. 154(b) by 0 days.

(21) Appl. No.: 16/824,895

(22) Filed: Mar. 20, 2020

(65) Prior Publication Data
US 2020/0271601 A1    Aug. 27, 2020

Related U.S. Application Data

(63) Continuation of application No. 16/251,909, filed on Jan. 18, 2019, which is a continuation-in-part of
(Continued)

(30) Foreign Application Priority Data

Jul. 19, 2016    (EP) .................... 16382350

(51) Int. Cl.
    *G01V 3/00*     (2006.01)
    *G01N 24/08*    (2006.01)
(Continued)

(52) U.S. Cl.
    CPC .......... *G01N 24/087* (2013.01); *G01N 24/08* (2013.01); *G01N 33/50* (2013.01); *G01R 33/4625* (2013.01); *G01R 33/4633* (2013.01)

(58) Field of Classification Search
    USPC .......................................... 324/309
    See application file for complete search history.

(56) References Cited

U.S. PATENT DOCUMENTS 7,968,082 B1    6/2011    Shriver
8,802,156 B2    8/2014    Franco Rodriguez
(Continued)

FOREIGN PATENT DOCUMENTS

EP    2213282 A1    4/2010
ES    2336297 B1    1/2011
(Continued)

OTHER PUBLICATIONS

Oliveira et al. (Structural and functional analyses of biosimilar enoxaparins available in Brazil in Thromb. Heamo. (2014), 113(1), 53-65.
(Continued)

*Primary Examiner* — Rodney E Fuller
(74) *Attorney, Agent, or Firm* — Innovar, L.L.C.; Rick Matos

(57) ABSTRACT

A nuclear magnetic resonance method of analysis for glycosaminoglycans in general, and of heparins and low molecular weight heparins and their derivatives in particular, is provided. The method allows for their identification and for relative quantification of respective characteristic signals by $^1$H-NMR and/or $^1$H-$^{13}$C HSQC.

31 Claims, 7 Drawing Sheets

Related U.S. Application Data application No. PCT/EP2017/068285, filed on Jul. 19, 2017.

(51) Int. Cl.
*G01R 33/46* (2006.01)
*G01N 33/50* (2006.01)

(56) References Cited

U.S. PATENT DOCUMENTS

| | | |
|---|---|---|
| 8,822,659 B2 | 9/2014 | Lopez-Belmonte Encina |
| 9,211,305 B2 | 12/2015 | Encina |
| 2004/0092037 A1 | 5/2004 | Sasisekharan |
| 2011/0201572 A1 | 8/2011 | Lopez-Belmonte Encina |
| 2011/0306757 A1 | 12/2011 | Lopez-Belmonte Encina |
| 2014/0066402 A1 | 3/2014 | Lopez-Belmonte Encina |

FOREIGN PATENT DOCUMENTS

| | | |
|---|---|---|
| ES | 2340902 B1 | 4/2011 |
| WO | 2010000904 A1 | 1/2010 |
| WO | 2010040880 A1 | 4/2010 |
| WO | 2010086425 A1 | 8/2010 |

OTHER PUBLICATIONS

Linhardt et al. ("Mapping and quantification of the major oligosaccharides component of heparin", in Biochem. J. (1988), 254, 781-787).

Tran et al. ("Anticoagulant therapy for major arterial and venous thromboembolism", in Basic principles and clinical practice (Colman RW, Marder VJ, Clowes AW, George JN, Goldhaber SZ (Ed). Lippincott Williams and Wilkins; 2006:1673-1688).

Xu et al. ("Chemoenzymatic synthesis of homogenous ultra low molecular weight heparins", in Science (2011), 334, 498-501).

Langeslay et al. ("Advancing Analytical Methods for Characterization of Anionic Carbohydrate Biopolymers", Langeslay D.J. PhD Thesis UC Riverside 2013).

Beni et al. ("Analysis and characterization of heparin impurities", in Anal. Bioanal. Chem. (2011), 399, 527-539).

Casu et al. ("Characterization of Sulfation Patterns of Beef and Pig Mucosal Heparins by Nuclear Magnetic Resonance", in Arzneim.-Forsch./Drug Res. (1996), 46, 472-477).

Keire et al. ("Characterization of currently marketed heparin products: composition analysis by 2D-NMR", in Anal. Methods (2013), 5, 2984-2994).

Ozug et al. ("Structural elucidation of the tetrasaccharide pool in enoxaparin sodium", in Anal. Bioanal. Chem. (2002), 403, 2733-2744).

Bisio et al. ("Structural features of low molecular weight heparins affecting their affinity to antithrombin", in Thromb. Hemost. (2009), 102, 865-873).

Guerrini et al. ("Low-molecular-weight heparins: structural differentiation by two-dimensional nuclear magnetic resonance spectroscopy", in Semin. Thromb. Hemost. (2007), 33, 478-487).

Malz et al. ("Validation of quantitative NMR", in Journal of Pharmaceutical and Biomedical Analysis (2005), 38, 813-823).

Glauser et al. ("Generic versions of enoxaparin available for clinical use in Brazil are similar to the original drug", in J. Thromb. Haemost. (2011), 9, 1419-1422).

Desai et al. ("Molecular Weight of Heparin using 13C Nuclear Magnetic Resonance Spectroscopy", in J. Pharm. Sci. (1995), 84(2), 212-215).

Mourier et al. ("Analytical and Statistical Comparability of Generic Enoxaparins from the US Market with the Originator Product", in J. Pharm. Biomed. Anal. (2015), 115(29), 431-442).

Franchini et al. ("The evolution of anticoagulant therapy", in Blood Trans. (2016), 14(2), 175-184).

Lima et al. ("Ultra-low-molecular-weight heparins: precise structural features impacting specific anticoagulant activities", in Thromb. Haemo. (2013), 109(3), 471-478).

METHOD FOR THE ANALYSIS OF GLYCOSAMINOGLYCANS, AND THEIR DERIVATIVES AND SALTS BY NUCLEAR MAGNETIC RESONANCE

CROSS-REFERENCE TO EARLIER FILED APPLICATIONS

The present application claims the benefit of and is a continuation of application Ser. No. 16/251,909 filed Jan. 18, 2019, which is a continuation-in-part of international application PCT/EP2017/068285 filed Jul. 19, 2017, which claims the benefit of European application EP 16382350.3 filed Jul. 19, 2016, the entire disclosures of which are hereby incorporated by reference.

FIELD OF THE INVENTION

The present invention concerns an analytical method employing nuclear magnetic resonance ($^1$H-NMR, $^{13}$C-NMR, and/or $^1$H-$^{13}$C-HSQC) for the characterization of glycosaminoglycans (GAG's), derivatives thereof, and/or salts thereof. The method allows for qualitative and quantitative analysis of the saccharides comprising said GAG's.

BACKGROUND OF THE INVENTION

Nuclear magnetic resonance (NMR) spectroscopy is one of the most important and widespread analytical techniques used in the characterization of glycosaminoglycans in general, and heparins and low molecular weight heparins and their derivatives in particular.

The possibility of performing both one-dimensional and two-dimensional experiments makes this technique highly sensitive for determining small variations in molecular structure, making it very advantageous for a suitable characterization of these compounds.

Glycosaminoglycans (GAGs) are linear and negatively charged polysaccharides with a weight-average molecular weight between 10-100 KDa ("The Structure of Glycosaminoglycans and their Interactions with Proteins"; Gandhi N S and Mancera R L. in *Chem. Biol. Drug Des.* (2008), 72, 455-482). There are two large groups (genera) of glycosaminoglycans: non-sulfated (such as hyaluronic acid) and sulfated (such as chondroitin sulfate, dermatan sulfate, keratan sulfate, heparin, and heparan sulfate). Glycosaminoglycan chains are formed by disaccharide units or disaccharides composed of an uronic acid (D-glucuronic or L-iduronic) and an amino sugar (D-galactosamine or D-glucosamine) such as the following.

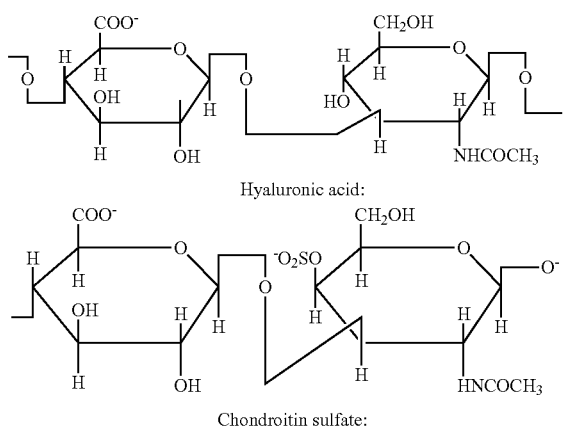

Hyaluronic acid:

Chondroitin sulfate:

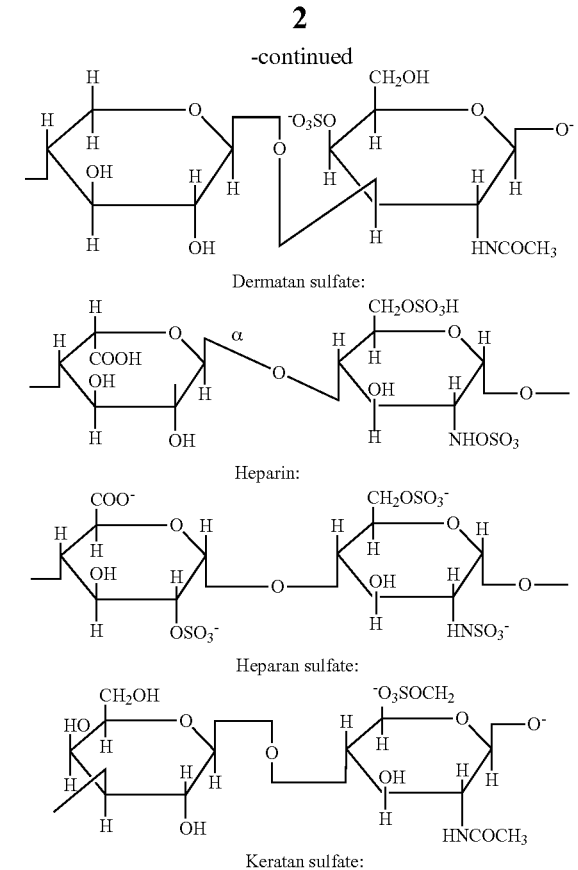

Dermatan sulfate:

Heparin:

Heparan sulfate:

Keratan sulfate:

Formula 1: General Structure of the Disaccharide Unit for the Different Types of Glycosaminoglycans.

Heparin is a polysaccharide of the glycosaminoglycan genus of compounds, formed by uronic acid (L-iduronic or D-glucuronic acid) and D-glucosamine, linked in alternating sequence. L-iduronic acid may be 2-O-sulfated and D-glucosamine may be N-sulfated and/or 6-O-sulfated, and to a lesser extent N-acetylated or 3-O-sulfated ("Mapping and quantification of the major oligosaccharides component of heparin", Linhardt R J, Rice K G, Kim Y S et al. in *Biochem. J.* (1988), 254, 781-787). The major disaccharide repeating unit corresponds to the trisulfated disaccharide, 2-O-sulfo-L-iduronic acid (1→4) 2-N-sulfo-6-O-sulfo-D-glucosamine.

The origin of this structural variability present in heparin oligosaccharide chains is found in their biosynthesis and in the mechanism regulating it. Thus, in the first stage of biosynthesis, a tetrasaccharide fragment formed by glucose-galactose-galactose-xylose is bound to a protein core, starting the biosynthesis of the glycoprotein chain. Next, glucuronic acid (GlcA) residues and N-acetylglucosamine (GlcNAc) residues are alternatively incorporated forming a polysaccharide chain of approximately 300 units. At the same as this chain elongation occurs, and due to the intervention of various enzymes, modifications occur therein. Thus, the action of N-deacetylase/N-sulfotransferase enzymes produce the N-deacetylation and N-sulfation of the GlcNAc units, turning them into N-sulfoglucosamine (GlcNS). A C5 epimerase catalyzes the transformation of certain units of GlcA into iduronic acid (IdoA), followed by a 2-O-sulfation due to action of a 2-O-sulfotransferase. Next, a 6-O-sulfotransferase, transfers a 6-O-sulfo group to GlcNS and GlcNAc units. Finally, a 3-O-sulfotransferase acts on certain N-sulfo-6-O-sulfoglucosamine (GlcNS6S) units generating N-sulfo-3,6-di-O-sulfoglucosamine (GlcNS3S6S) residues.

The apparently random and incomplete nature of the initial N-deacetylation is what is mainly responsible for the introduction of the structural heterogeneity in heparin in the first phase of its biosynthesis. Structural variability with regard to the degree and positions of sulfation is the result of the incomplete nature of modifications made by the biosynthetic enzymes that lead to the production of heparin sodium molecules with a variable disaccharide substitution pattern. Currently, no prior art NMR method nor corresponding composition for the highly accurate quantification of individual saccharides in GAG's and heparin molecules exist.

Heparin is preferably used as sodium salt, but it can also be used as a salt of other alkaline or alkaline-earth metals and is mainly used as antithrombotic and anticoagulant medicine ("Anticoagulant therapy for major arterial and venous thromboembolism", Tran HAM, Ginsberg J S in *Basic principles and clinical practice* (Colman R W, Marder V J, Clowes A W, George J N, Goldhaber S Z (Ed). Lippincott Williams and Wilkins; 2006:1673-1688)).

Heparins can be classified depending on their molecular weight: unfractionated heparin (UFH), Low Molecular Weight Heparin (LMWH) with a weight-average molecular weight lower than 8000 Da and Ultra Low Molecular Weight Heparin (ULMWH) with a weight-average molecular weight lower than 3000 Da ("Chemoenzymatic synthesis of homogenous ultra low molecular weight heparins", Xu Y. et al. in *Science* (2011), 334, 498-501). LMWH and ULMWH come from depolymerization of the original molecule of UFH, and its manufacturing process may introduce certain process-related characteristics in the molecule's structure. Thus, the resulting molecule's structure derives on the one hand from the structure of the heparin used as starting material and on the other hand from the characteristic residues generated during preparation and characteristic manufacturing method used.

The manufacturing process of enoxaparin sodium (β-elimination by alkaline treatment on benzyl ester of heparin in aqueous medium) and bemiparin sodium (β-elimination by alkaline treatment in non-aqueous medium) generates as the majority species at the ends 4,5-unsaturated-2-O-sulfo-uronic acid (ΔU2S), at the non-reducing end, and 2-N-sulfo-6-O-sulfoglucosamine, at the reducing end of the molecule. Additionally, the non-reducing end may have saccharides such as 4,5-unsaturated-2-O-uronic acid (ΔU). At the reducing end of the aforementioned residue, it is possible to find 2-N-sulfo-6-O-sulfomannosamine (the alkaline treatment catalyzes the epimerization in C2), in addition to another two species of 1,6-anhydro derivatives: 2-N-sulfo-1,6-anhydroglucosamine (1,6-an.A) and 2-N-sulfo-1,6-anhydro-mannosamine (1,6-an.M).

Formula 2: Structures Present at the Reducing and Non-Reducing End in Enoxaparin and Bemiparin Sodium.

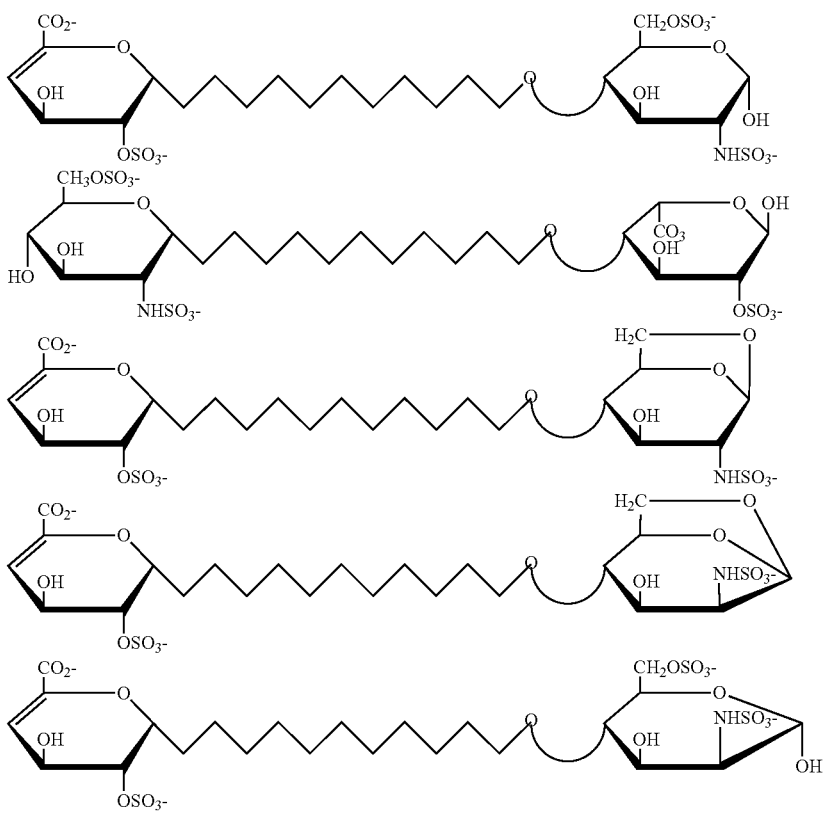

Residues are also generated in other low molecular weight heparins according to their manufacturing process. For example, tinzaparin sodium, which is obtained by a method of β-elimination by treatment with heparinases, has at its non-reducing end 4,5-unsaturated-2-O-sulfouronic acid (ΔU2S).

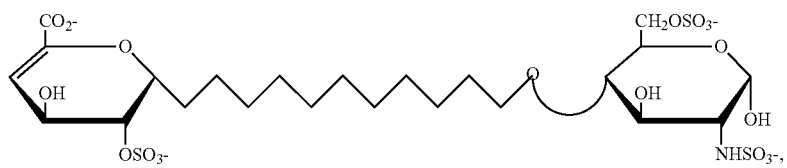

Formula 3: Structures Present at the Reducing and Non-Reducing End in Tinzaparin Sodium.

Dalteparin sodium is obtained by treatment with nitrous acid which generates a 2,5-anhydro-mannitol residue at the reducing end of the molecule.

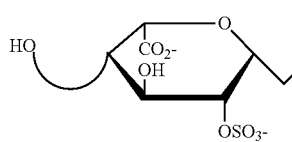

Formula 4: Structures present at the reducing and non-reducing end in dalteparin sodium.

NMR spectroscopy allows for identification of the saccharide residues typically present in heparin and low molecular weight heparin, such as those formed during respective manufacturing processes.

One of the advantages associated with the use of NMR for structural characterization is that, for its analysis, the samples do not require previous derivatization or chromatographic fractionation. In other words, the sample can be directly analysed by NMR, without the need for intermediate treatments.

NMR spectroscopy is used to determine the sequence of monosaccharide residues present in these compounds and unequivocally determines the N-acetylation and N- and O-sulfation points throughout the oligosaccharide chain. Additionally, this technique allows specifically determining the orientation of the anomeric bonds and distinguishing between the iduronic acid of glucuronic acid epimers. ("Advancing Analytical Methods for Characterization of Anionic Carbohydrate Biopolymers", Langeslay D. J. PhD Thesis UC Riverside 2013). However, given the high degree of microheterogeneity and polydispersity of these compounds, the complete characterization of heparins and low molecular weight heparins is currently still a challenge.

NMR can also be used to obtain information on those structural residues associated with the production process of heparins and of low molecular weight heparins, such as the state of epimerization of uronic acids (iduronic acid vs. glucuronic acid), ratio of sulfated and nonsulfated 4,5-uronate residues at the non-reducing end (for low molecular weight heparins produced by a β-elimination method or treatment with heparinases).

Likewise, NMR can be used as a screening technique to determine impurities present in glycosaminoglycans ("Analysis and characterization of heparin impurities", Beni S. et al. in *Anal. Bioanal. Chem.* (2011), 399, 527-539).

Various NMR methods and experiments have been disclosed for the structural characterization of glycosaminoglycans in general, and heparins and low molecular weight heparins in particular. Thus, for example, $^{13}$C-NMR spectroscopy has been used to determine the degree of sulfation in heparin sodium of different animal origin ("Characterization of Sulfation Patterns of Beef and Pig Mucosal Heparins by Nuclear Magnetic Resonance", Casu B. et al. in *Arzneim.-Forsch./DrugRes.* (1996), 46, 472-477).

$^{1}$H-NMR spectroscopy has been the most widely used technique for the study of these compounds, since $^{1}$H is an abundant nucleus with a high gyromagnetic ratio. The region between 1.8-2.1 ppm comprises the signals corresponding to the N-acetyl groups or methyl groups of the reducing ends which may be synthetically included. The region between 2.8-4.5 ppm comprises the majority of the saccharide ring signals and has a high degree of overlapping between them, which makes it difficult to extract structural information directly from this area.

Two-dimensional experiments (2D NMR) allow the shortcomings of one-dimensional experiments to be overcome, i.e. shortcomings such as the overlapping of signals. Two-dimensional spectra have two frequency dimensions and another signal intensity which allows them to become a powerful tool for assigning oligosaccharide structures derived from heparin ("Characterization of currently marketed heparin products: composition analysis by 2D-NMR", Keire D. A. et al. in *Anal. Methods* (2013), 5, 2984-2994).

TOCSY (TOtal Correlation SpectroscopY) spectroscopy can be used for the structural analysis of oligosaccharides, since the information obtained in that type of experiment allows the correlation of nuclei found in the same spin system, in this case all the protons within the same monosaccharide.

Another two-dimensional experiment of particular importance for the structural characterization of this type of compounds is 1H-$^{13}$C HSQC (Heteronuclear Single-Quantum Correlation), which correlates $^{1}$H proton chemical shifts with chemical shifts of $^{13}$C and permits assignment of the primary structures of oligosaccharides derived from GAGs (glycosaminoglycans) and the monosaccharide composition ("Structural elucidation of the tetrasaccharide pool in enoxaparin sodium", Ozug J. et al. in *Anal. Bioanal. Chem.* (2002), 403, 2733-2744; "Structural features of low molecular weight heparins affecting their affinity to antithrombin", Bisio A. et al. in *Thromb. Hemost.* (2009), 102, 865-873).

The increase in spectral dispersion achieved with this two-dimensional technique allows the quantification of the integrals of the signals which are superimposed in the corresponding one-dimensional spectra ("Low-molecular-weight heparins: structural differentiation by two-dimensional nuclear magnetic resonance spectroscopy", Guerrini M. et al. *Semin. Thromb. Hemost.* (2007), 33, 478-487).

Nuclear magnetic resonance is a quantitative spectroscopy technique, since the intensity (amplitude) of the resonance lines is directly proportional to the number of resonant nuclei (spin). This, in principle, makes it possible to precisely determine the quantity of molecular structures.

The increase in intensity of the magnetic fields used in NMR has allowed the limits of detection to significantly be reduced. However, the absence of precise methods that consider and control both the experimental methods and the processing and evaluation of the spectra means that measurements made on identical samples in various laboratories may significantly differ ("Validation of quantitative NMR", Malz F. and Jancke H. in *Journal of Pharmaceutical and Biomedical Analysis* (2005), 38, 813-823).

The complexity of the nuclear magnetic resonance spectra of glycosaminoglycans in general, and heparins and low molecular weight heparins and their derivatives in particular, has meant that to date no specific validation methods have been developed which allow quantification of its characteristic signals, and therefore, the suitable characterization and differentiation of these compounds. In other words, prior art NMR methods have not successfully achieved highly accurate quantitation of each of the individual saccharide residues present GAG's and heparins.

With regard to GAG pharmaceutical products, their approval by health authorities of biosimilars and/or generics significantly differ from one another, which clearly indicates that they are inadequate methods ("Generic versions of enoxaparin available for clinical use in Brazil are similar to the original drug", Glauser B. F., Vairo B. C., Oliveira C. P. M., Cinelli L. P., Pereira M. S. and Mourao P. A. S. in *J. Thromb. Haemost.* (2011), 9, 1419-1422).

SUMMARY OF THE INVENTION

It is an object of the present invention to overcome shortcomings of prior NMR methods for analysis of GAG's. The present inventors have developed a method which enables unequivocal differentiation of GAG's from one another. As a result, the percentage values of monosaccharide composition provided by the present invention make it possible to differentiate between low molecular weight GAG's obtained by different manufacturing processes and other molecular weight species of GAG's.

The present invention is useful for analysis of native forms of GAG's, modified forms of GAG's, as well as derivatives, free acid forms, and salt forms thereof. As used herein, the term glycosaminoglycan (GAG) is taken to mean at least the subgenera heparin sulfate, heparan sulfate, chondroitin sulfate, dermatan sulfate, keratan sulfate, hyaluronic acid, others described herein, as well as derivatives, free acid forms, and salt forms thereof.

Some of said subgenera are characterized as follows.

| Name | Hexuronic acid/ Hexose | Hexosamine | Linkage geometry between predominant monomeric units |
|---|---|---|---|
| Chondroitin sulfate | GlcUA or GlcUA(2S) | GalNAc or GalNAc(4S) or GalNAc(6S) or GalNAc(4S,6S) | 'GlcUAβ1-3'GalNAcβ1-4 |
| Dermatan sulfate | GlcUA or IdoUA or IdoUA(2S) | GalNAc or GalNAc(4S) or GalNAc(6S) or GalNAc(4S,6S) | 'IdoUAβ1-3'GalNAcβ1-4 |
| Keratan sulfate | Gal or Gal(6S) | GlcNAc or GlcNAc(6S) | -Gal(6S)β1-4GlcNAc(6S)β1-3 |
| Heparin | GlcUA or IdoUA(2S) | GlcNAc or GlcNS or GlcNAc(6S) or GlcNS(6S) | -IdoUA(2S)α1-4GlcNS(6S)α1-4 |
| Heparan sulfate | GlcUA or IdoUA or IdoUA(2S) | GlcNAc or GlcNS or GlcNAc(6S) or GlcNS(6S) | -GlcUAβ1-4GlcNAcα1-4 |
| Hyaluronan | GlcUA | GlcNAc | -GlcUAβ1-3GlcNAcβ1-4 | of certain low molecular weight heparins, as is the case of Enoxaparin sodium, requires confirmation of similarity between the biosimilar/generic and the reference listed drug (RLD). Similarity requires demonstration, among other aspects, of a suitable degree of structural similarity between both products. One of the basic aspects on a structural level that it is necessary to demonstrate is that the relative proportion of the monosaccharides that form their oligosaccharide chains and after statistical evaluation, fulfil biosimilarity criteria. For them, the method of the present invention is especially selective.

The present inventors have verified that, although the structural characterization by nuclear magnetic resonance has been widely used for characterization of these compounds, the state of the art provides no quantitative analysis methods of glycosaminoglycan analysis by means of NMR. The absence of these methods prevents the suitable comparability between identical samples studied and assessed under not suitably established experimental conditions.

Thus, it is possible to find in the literature publications wherein the values of relative proportion which are provided for the different component residues of these compounds Suitable specific GAG's that can be employed in or characterized by the invention are also selected from the group consisting of unfractionated heparin (UFH), Low Molecular Weight Heparin (LMWH) with a weight-average molecular weight lower than 8000 Da and Ultra Low Molecular Weight Heparin (ULMWH) with a weight-average molecular weight lower than 3000 Da, enoxaparin, dalteparin, bemiparin, tinzaparin, all other known GAG's, all GAG's described herein, as well as derivatives, free acid forms, and salt forms thereof.

Suitable GAG's that can be employed in or characterized by the invention are also selected from the group consisting of heparin, heparan, hyaluronan, keratan, dermatan, chondroitin, enoxaparin, bemiparin, dalteparin, tinzaparin, a salt of any of the preceding, a derivative of any of the preceding, a sulfated form of any of the preceding, a non-sulfated form of any of the preceding, an ultra-low molecular weight form of any of the preceding, a low molecular weight form of any of the preceding, a high molecular weight form of any of the preceding, an unfractionated form of any of the preceding, a fractionated form of any of the preceding, and a combination of any two or more thereof.

The present invention provides a NMR method of determining the relative content of individual saccharide residues forming a respective GAG. In some embodiments, the invention further comprises determining identity of individual saccharide residues forming a respective GAG. In some embodiments, the invention further provides a method of providing a chemical shift pattern for a GAG.

The invention provides a method for quantification of the characteristic signals of glycosaminoglycans in general (and heparins and low molecular weight heparins and their derivatives in particular) through the use of one-dimensional nuclear magnetic resonance of $^1$H-NMR and/or two-dimensional nuclear magnetic resonance of $^1$H-$^{13}$C HSQC. The present method employs quantification of characteristic $^1$H and $^{13}$C chemical shift signals for determination of the monosaccharide (saccharide residue) content in oligosaccharide and polysaccharides of GAG's and heparins.

In the chemical shift range of 4.5-6.0 ppm for $^1$H-NMR, the chemical shift signals corresponding to the anomeric protons are found. Since it is an area much less populated with signals, it is possible to extract a great deal of information from it. Furthermore, in the case of LMWHs obtained using a β-elimination mechanism, the range also contains the signals corresponding to H4 of the non-reducing ends of the molecule.

In some embodiments, the hydrogen of the saccharide being quantified is selected from the group consisting of the H1 hydrogen, H2 hydrogen, H3 hydrogen, H4 hydrogen, H5 hydrogen, and H6 hydrogen of the corresponding C1, C2, C3, C4, C5, and C6 carbons of the saccharide. In some embodiments, the chemical shift signal range for the hydrogen being quantified is in the range of 3.2 to 6 ppm, 4.5-6.0 ppm, or 3.2 to less than 4.5 ppm.

In some embodiments, the carbon of the saccharide being quantified is selected from the group consisting of the C1 carbon, C2 carbon, C3 carbon, C4 carbon, C5 carbon and C6 carbon of the saccharide. In some embodiments, the chemical shift signal range for the carbon being quantified is in the range of about 55 to about 115 ppm or about 25-25 ppm.

An aspect of the invention provides a $^1$H-NMR one-dimensional nuclear magnetic resonance and/or $^1$H-$^{13}$C HSQC two-dimensional nuclear magnetic resonance method for the analysis of a composition comprising saccharide residues present in, or derived from, GAG, the method comprising the steps of:
a) providing a composition comprising DMMA (dimethyl malonic acid or deuterated derivative thereof), at least one deuterated solvent, and at least one glycosaminoglycan comprising saccharide residues comprising respective anomeric hydrogens;
b) conducting at least one NMR analysis on said composition, wherein said at least one NMR analysis is selected from the group consisting of H-NMR one-dimensional analysis and $^1$H-$^{13}$C HSQC two-dimensional analysis, and wherein said DMMA is employed as an internal reference for concentration dependent response of chemical shift signal intensity for $^1$H and/or $^{13}$C, thereby providing at least one respective spectrum (numerical and/or graphical spectrum) comprising respective chemical shift signals for said respective anomeric hydrogens;
c) normalizing said respective chemical shift signals for said respective anomeric hydrogens with respect to the $^1$H and/or $^{13}$C chemical shift signal of said DMMA;
d) correlating said respective chemical shift signals for respective anomeric hydrogens to one or more reference chemical shift signals for respective anomeric hydrogens of reference saccharides selected from the group consisting of: 4,5-unsaturated 2-O-sulfo-uronic acid (ΔU2S), 4,5-unsaturated uronic acid (ΔU), 2-N-sulfo-1,6-anhydroglucosamine (1,6-an.A), 2-N-sulfo-1,6-anhydro-mannosamine (1,6-an.M), 2-N-sulfo-6-O-sulfoglucosamine (ANS6S), 2,5-anhydro mannitol, N-sulfoglucosamine, glucuronic acid, N-sulfo-6-O-sulfoglucosamine, 2-O-sulfoiduronic acid, iduronic acid, N-sulfo-3-O-sulfoglucosamine, N-sulfo-3,6-di-O-sulfoglucosamine, galacturonic acid, xylose, N-acetylglucosamine and N-acetyl-6-O-sulfoglucosamine, thereby providing the identity and relative proportion of individual saccharide residues present in said GAG.

The invention also provides a nuclear magnetic resonance (NMR) method for quantifying content of saccharide in one or more glycosaminoglycans in a composition, the method comprising at least the step of:
providing a composition comprising: i) at least one glycosaminoglycan (GAG) comprising plural saccharides comprising respective anomeric or target hydrogen atoms exhibiting respective anomeric or target $^1$H chemical shift signals when analyzed by NMR and further comprising respective anomeric or target carbon atoms covalently bound to said anomeric or target hydrogens atoms and exhibiting respective anomeric or target $^{13}$C chemical shift signals when analyzed by NMR;
ii) at least one reference compound comprising a hydrogen atom having a NMR signal T1 longitudinal relaxation time of 1 s or less and a respective carbon atom covalently bound to said hydrogen atom, wherein the at least one reference compound exhibits a reference $^1$H NMR chemical shift signal separated from said anomeric or target $^1$H chemical shift signals and further exhibits a reference $^{13}$C NMR chemical shift signal separated from said anomeric or target $^{13}$C chemical shift signals, and said reference $^1$H chemical shift signal and said reference $^{13}$C chemical shift signal each exhibits a concentration dependent intensity; and iii) at least one deuterated solvent for said glycosaminoglycan and said at least one reference compound.

In some embodiments, the method further comprises comparing the at least one respective spectrum for a sample GAG to at least one reference spectrum for a reference GAG, said spectra having been obtained under substantially the same conditions.

The method can further comprise: a) comparing the intensities of said anomeric or target $^1$H chemical shift signals to the intensity of the reference $^1$H chemical shift signal; b) comparing the intensities of said anomeric or target $^{13}$C chemical shift signals to the intensity of the reference $^{13}$C chemical shift signal; or c) a combination of a) and b).

The method can further comprise: a) obtaining the integrals for said anomeric or target $^1$H chemical shift signals and said reference $^1$H chemical shift signal; b) obtaining the integrals for said anomeric or target $^{13}$C chemical shift signals and said reference $^{13}$C chemical shift signal; or c) a combination of a) and b).

The method can further comprise: a) dividing said integrals for said anomeric or target $^1$H chemical shift signals by the integral of said reference $^1$H chemical shift signal to provide normalized values of said integrals for said anomeric or target $^1$H chemical shift signals; b) dividing said integrals for said anomeric or target $^{13}$C chemical shift signals by the integral of said reference $^{13}$C chemical shift signal to provide normalized values of said integrals for said anomeric or target $^{13}$C chemical shift signals; or c) a combination of a) and b).

As used herein, the term "anomeric carbon" refers to a carbon atom having an anomeric hydrogen covalently bound thereto.

The method can further comprise: a) determining the relative proportions of said anomeric or target hydrogens with respect to the total amount of anomeric or target hydrogens present in said glycosaminoglycan to provide the content of saccharide in said one or more glycosaminoglycans; b) determining the relative proportions of said anomeric or target carbons with respect to the total amount of anomeric or target carbons present in said glycosaminoglycan to provide the content of saccharide in said one or more glycosaminoglycans; or c) a combination of a) or b).

The method can further comprise: a) correlating the relative proportions of said anomeric or target hydrogens with the relative proportions of corresponding saccharides present in said glycosaminoglycan; b) correlating the relative proportions of said anomeric or target carbons with the relative proportions of corresponding saccharides present in said glycosaminoglycan; or c) a combination of a) or b).

The method can further comprise: a) developing a calibration curve for said at least one glycosaminoglycan; b) developing a calibration curve for said at least one reference compound; c) developing calibration curves for said plural saccharides; or d) a combination of any two or more of the above.

The method can further comprise: providing a reference $^1$H NMR spectrum and/or reference $^{13}$C NMR spectrum for each of said plural saccharides being quantified.

The method can further comprise: providing a reference $^1$H-NMR spectrum and/or reference $^{13}$C-NMR spectrum for said at least one glycosaminoglycan.

The method can further comprise: a) determining the relative proportions of anomeric or target hydrogens in one or more reference glycosaminoglycans; b) determining the relative proportions of anomeric or target carbons in one or more reference glycosaminoglycans; or c) a combination of a) or b).

The method can further comprise: a) correlating said relative proportions of anomeric or target hydrogens with the relative proportions of corresponding saccharides present in said one or more reference glycosaminoglycans; b) correlating said relative proportions of anomeric or target carbons with the relative proportions of corresponding saccharides present in said one or more reference glycosaminoglycans; or c) a combination of a) or b).

The suitable quantification of the characteristic signals of these products and of their monosaccharide composition or characteristic residues, allows for differentiation of polysaccharides from one another, and in the case of the low molecular weight heparins, to confirm that the products have been manufactured according to the declared method.

This quantification of the residues is obtained in percentage values and in relative form to the complete structure of each heparin thereby providing a characteristic chemical shift spectrum (NMR fingerprint) of each one of the structures and allowing for an unequivocal deduction and identification both of the GAG analyzed and of the process by which it was prepared. Accordingly, the NMR method of present invention can be used as both a quality control system (i.e. a method to determine whether the GAG analyzed corresponds to a reference GAG or has been adulterated) and/or as a method for the identification of new GAG's.

With the aim of establishing a selective quantitative method to determine the proportion of the signals corresponding to these residues present in the structure of these compounds, which allows the suitable comparison between results and which makes it possible to avoid the error associated to the conditions in which NMR experiments are performed, the inventors have found that the use of dimethylmalonic acid (DMMA) as internal standard in $^1$H-NMR and $^1$HSQC analyses for the relative quantification of the signals corresponding to the different component monosaccharides is suitable, since among other aspects it has a longitudinal relaxation time (T1) of under 1 second similar to the T1 of the anomeric protons and carbons ("Molecular Weight of Heparin using 13C Nuclear Magnetic Resonance Spectroscopy", Desai U. R. and Linhardt R. J., in *J. Pharm. Sci.* (1995), 84(2), 212-215), which allows a good transfer of polarization and, therefore, an increase in intensity of the signals, which makes it suitable for this purpose.

Thus, in some embodiments, the instant method for NMR analysis (H-NMR and/or $^1$H-$^{13}$C HSQC), of GAG's employs DMMA as internal standard for the quantification of the characteristic signals of said GAG's. Surprisingly, it has been found that the selection DMMA allows for quantitative determination, by percentage means or relative proportion, of the characteristic signals in glycosaminoglycans, in particular those typically related to heparins. The method provides high specificity, high accuracy, high repeatability (reproducibility) and high linearity (in a certain concentration range for DMMA) between the chemical shift signal intensity and the concentration of the characteristic residues of the target GAG's, thereby enabling development of a quantitative analytical method for said GAG's. The use of DMMA is particularly preferred because of the combination of at least the following properties: a) solubility in solvent(s) in which the GAG is soluble; b) a $^1$H reference chemical shift signal separated from the target $^1$H chemical shift signals of the GAG; c) a $^{13}$C reference chemical shift signal separated from the target $^{13}$C chemical shift signals of the GAG; d) a linear relationship between concentration of DMMA and reference chemical shift signal(s) intensity at a concentration that is acceptable for GAG-containing samples; e) substantial independence of said linear relationship upon presence or absence of GAG; and f) lack of degradation of GAG by DMMA during NMR analysis under experimental conditions employed.

In some aspects, the invention provides a nuclear magnetic resonance (NMR) method for quantifying the content of saccharide(s) in one or more glycosaminoglycans in a composition, the method comprising at least the step of providing a composition comprising: i) at least one glycosaminoglycan (GAG) comprising plural saccharides comprising respective anomeric hydrogen atoms exhibiting respective anomeric $^1$H and/or $^{13}$C chemical shift signals when analyzed by NMR; ii) at least one reference compound comprising a hydrogen atom having a NMR signal T1 (longitudinal relaxation time) of about 1 s or less, wherein the at least one reference compound exhibits a reference $^1$H-NMR chemical shift signal separated from said anomeric $^1$H chemical shift signals, and said reference $^1$H chemical shift signal exhibits a concentration dependent intensity (or amplitude); and iii) at least one deuterated solvent for said glycosaminoglycan and said at least one reference compound.

Embodiments of the invention provide a composition comprising: a) at least one glycosaminoglycan (GAG) comprising plural saccharides comprising respective target hydrogen atoms and respective carbon atoms exhibiting respective target $^1$H and/or $^{13}$C chemical shift signals when analyzed by NMR; b) at least one reference compound comprising a hydrogen atom having a NMR signal T1 longitudinal relaxation time of about 1 s or less, wherein the at least one reference compound exhibits a reference $^1$H-NMR chemical shift signal separated from said target $^1$H chemical shift signals, and said reference $^1$H chemical shift signal exhibits a concentration dependent intensity (or amplitude); and iii) at least one deuterated solvent for said glycosaminoglycan and said at least one reference compound.

Embodiments of the invention provide a composition comprising: a) at least one GAG present at a concentration of about 0.005 to about 1 mg/L, about 0.01 mg/L to about 0.5 mg/L, or about 0.02 to about 0.2 mg/L; b) DMMA present at a concentration of about 0.05 to about 5 mM, about 0.1 to about 5 mM, about 0.1 to about 4 mM, about 0.1 to about 3 mM, or about 0.2 to about 2.5 mM; and c) at least one deuterated solvent.

The method can further comprise conducting at least one NMR analysis, on said composition, selected from the group consisting of one-dimensional (1D)$^1$H-NMR analysis, two-dimensional (2D)$^1$H-$^{13}$C-NMR analysis, or a combination of said analyses, to provide at least one GAG NMR spectrum. Said at least one NMR analysis comprises exposing said composition to plural magnetic pulses such that the time between individual magnetic pulses (d1) is about the T1 or more of the target H being analyzed, or is about one second or more, or about 1 s to about 10 s, or about 1 s to about 5 s, or about 1 s to about 2 s. In some embodiments, the target H is an anomeric hydrogen atom of a saccharide residue.

The method can further comprise comparing the intensities of said anomeric or target $^1$H chemical shift signals to the intensity of the reference $^1$H chemical shift signal.

The method can further comprise comparing the intensities of said anomeric or target $^{13}$C chemical shift signals to the intensity of the reference $^{13}$C chemical shift signal.

The method can further comprise normalizing the intensities of said anomeric or target $^1$H chemical shift signals relative to the intensity of the reference $^1$H chemical shift signal.

The method can further comprise normalizing the intensities of said anomeric or target 13C chemical shift signals relative to the intensity of the reference $^{13}$C chemical shift signal.

The method can further comprise obtaining the integrals for said anomeric or target $^1$H chemical shift signals and said reference $^1$H chemical shift signal. Said integrals for said anomeric or target $^1$H chemical shift signals can be divided by the integral of said reference $^1$H chemical shift signal to provide normalized values of said integrals for said anomeric or target $^1$H chemical shift signals. The method can further comprise determining the relative proportions of said anomeric or target hydrogens with respect to the total amount of anomeric or target hydrogens present in said glycosaminoglycan to provide the content of saccharide in said one or more glycosaminoglycans.

The method can further comprise correlating the relative proportions of said anomeric or target hydrogens with the relative proportions of corresponding saccharides present in said glycosaminoglycan.

The method can further comprise: a) developing a calibration curve for said at least one glycosaminoglycan; b) developing a calibration curve for said at least one reference compound; c) developing calibration curves for said plural saccharides; or d) a combination of any two or more of the above.

The method can further comprise providing a reference $^1$H-NMR spectrum and/or reference $^{13}$C-NMR spectrum for each of said plurals saccharides being quantified The method can further comprise determining the relative proportions of anomeric or target hydrogens in one or more reference glycosaminoglycans. The method can further comprise correlating said relative proportions of anomeric or target hydrogens with the relative proportions of corresponding saccharides present in said one or more reference glycosaminoglycans.

The method can further comprise embodiments, wherein said concentration dependent intensity is substantially linear in the range of about 0.2 mM to about 2.5 mM of said at least one reference compound. The linearity can have a correlation coefficient ($R^2$) of ≥0.90, ≥0.95, ≥0.98, or ≥0.99.

The method can further comprise using the singlet $^1$H-NMR chemical shift of 3-(trimethylsilyl)-priopionic-D4 acid as a chemical shift reference for 0 ppm.

The method can further comprise embodiments, wherein the two-dimensional $^1$H-$^{13}$C-NMR analysis is heteronuclear single-quantum correlation (HSQC).

Other aspects of the invention provide a composition comprising:
1) at least one glycosaminoglycan comprising at least one saccharide comprising anomeric or target hydrogen exhibiting respective anomeric or target $^1$H chemical shift signal in the range of about 4.5 to about 6 ppm or about 3.2 to about 6 ppm when analyzed by NMR;
2) at least one reference compound comprising at least one reference hydrogen atom having a NMR signal T1 (longitudinal relaxation time) of about 1 s or less, wherein the at least one reference hydrogen exhibits a reference $^1$H NMR chemical shift signal separated from said anomeric or target $^1$H chemical shift signals, and said reference $^1$H chemical shift signal exhibits a concentration dependent signal intensity; and
3) at least one deuterated solvent for said glycosaminoglycan and said at least one reference compound.

The invention also provides embodiments wherein said glycosaminoglycan is an oligosaccharide or polysaccharide.

The invention also provides embodiments wherein the deuterated solvent is selected from the group consisting of any deuterated solvent in which the GAG is soluble at the concentration range described herein, any combination of deuterated solvents in which the GAG is soluble at the concentration range described herein, $D_2O$, $CD_3CO_2D$, $CD_3OD$, $CCl_3OD$, $(CD_3)_2SO$, $CD_3CN$, $(CD_3)_2NC(O)D$, and a combination of $D_2O$ and at least one other deuterated solvent. In some embodiments, said at least one other deuterated solvent is selected from the group consisting of $CD_3CO_2D$, $CD_3OD$, $CCl_{30}D$, $(CD_3)_2SO$, $CD_3CN$, and $(CD_3)_2NC(O)D$. Deuterated mineral acid and/or alkali can be used to adjust the pH of the composition as needed.

The invention also provides embodiments wherein the at least one saccharide is selected from the group consisting of 4,5-unsaturated 2-O sulfo-uronic acid (ΔU2S), 4,5-unsaturated uronic acid (ΔU), 2-N-sulfo-1,6-anhydroglucosamine (1,6-an.A), 2-N-sulfo-1,6-anhydro-mannosamine (1,6-an.M), 2-N-sulfo-6-O-sulfoglucosamine (ANS6S), 2,5-anhydro mannitol, N-sulfoglucosamine, glucuronic acid, N-sulfo-6-O-sulfoglucosamine, 2-O-sulfoiduronic acid, iduronic acid, N-sulfo-3-O-sulfoglucosamine, N-sulfo-3,6-di-O-sulfoglucosamine, galacturonic acid, Xylose, N-acetylglucosamine and N-acetyl-6-O-sulfoglucosamine.

The invention also provides embodiments wherein said at least one reference compound is present at a concentration in the range of about 0.2 mM to about 2.5 mM.

The invention also provides embodiments wherein said reference $^1$H-NMR chemical shift signal is outside the range of about 4.5 to about 6.0 ppm or outside the range of about 3.2 to about 6 ppm.

The invention also provides embodiments wherein said at least one internal reference compound exhibits a reference $^1$H-NMR chemical shift signal within the range of about 1.2 ppm to about 1.7 ppm, about 1.2 ppm to about 1.6 ppm, about 1.2 to about 1.5 ppm, about 1.3 to about 1.5 ppm, about 1.4 to about 1.5 ppm, about 1.3 ppm, and about 1.4 ppm, each said range and value being inclusive of the range limits especially as defined by the definition of the term "about" as used herein, and each said chemical shift being relative to TSP as defining 0 ppm. In some embodiments, said reference $^1$H-NMR chemical shift signal is a singlet.

In some embodiments, said at least one internal reference compound exhibits a reference $^1$H-NMR chemical shift signal of greater than 0 ppm and less than about 1.8 ppm, within the range of about 2.2 to about 3 ppm, or within the range of about 6.2 to about 7.2 ppm, each said range and value being inclusive of the range limits especially as defined by the definition of the term "about" as used herein, and each said chemical shift being relative to TSP as defining 0 ppm.

The invention also provides embodiments wherein said at least one internal reference compound exhibits a $^{13}$C-NMR chemical shift signal within the range of about 25 to about 27 ppm or within the range of about 26 ppm to about 27 ppm, inclusive of the range limits especially as defined by the definition of the term "about" as used herein, and each said chemical shift being relative to TSP as defining 0 ppm. In some embodiments, said reference $^{13}$C-NMR chemical shift signal is a singlet. In some embodiments, the reference $^{13}$C-NMR chemical shift signal is in the range of greater than 0 pp to less than 22 ppm, or 25 ppm to less than 55 ppm.

The invention also provides embodiments wherein said reference $^1$H-NMR chemical shift is relative to the singlet chemical shift of 3-(trimethylsilyl)-priopionic-D4 acid assigned as 0 ppm.

The invention also provides embodiments wherein said at least one reference compound is dimethylmalonic acid (DMMA), derivative thereof, salt thereof or combination of any two or more thereof.

The invention also provides embodiments wherein said at least one reference compound is present at a known or predetermined concentration or amount.

The invention provides embodiments wherein said at least one glycosaminoglycan is present at a known or predetermined concentration or amount.

The invention also provides embodiments wherein said at least one glycosaminoglycan is selected from the group consisting of heparin, heparan, enoxaparin, bemiparin, dalteparin, tinzaparin, a salt of any of the preceding, a derivative of any of the preceding, or a combination thereof. The method and composition of the invention are suitable for use in quantifying sulfated and/or non-sulfated saccharides present in glycosaminoglycans.

Another aspect of the invention provides a software program for conducting one or more of the methods disclosed herein. Another aspect of the invention provides a NMR spectrometer controlled by said software or with said software installed therein. Another aspect of the invention provides computer with said software installed therein.

ABBREVIATIONS AND ACRONYMS

Figure 1:
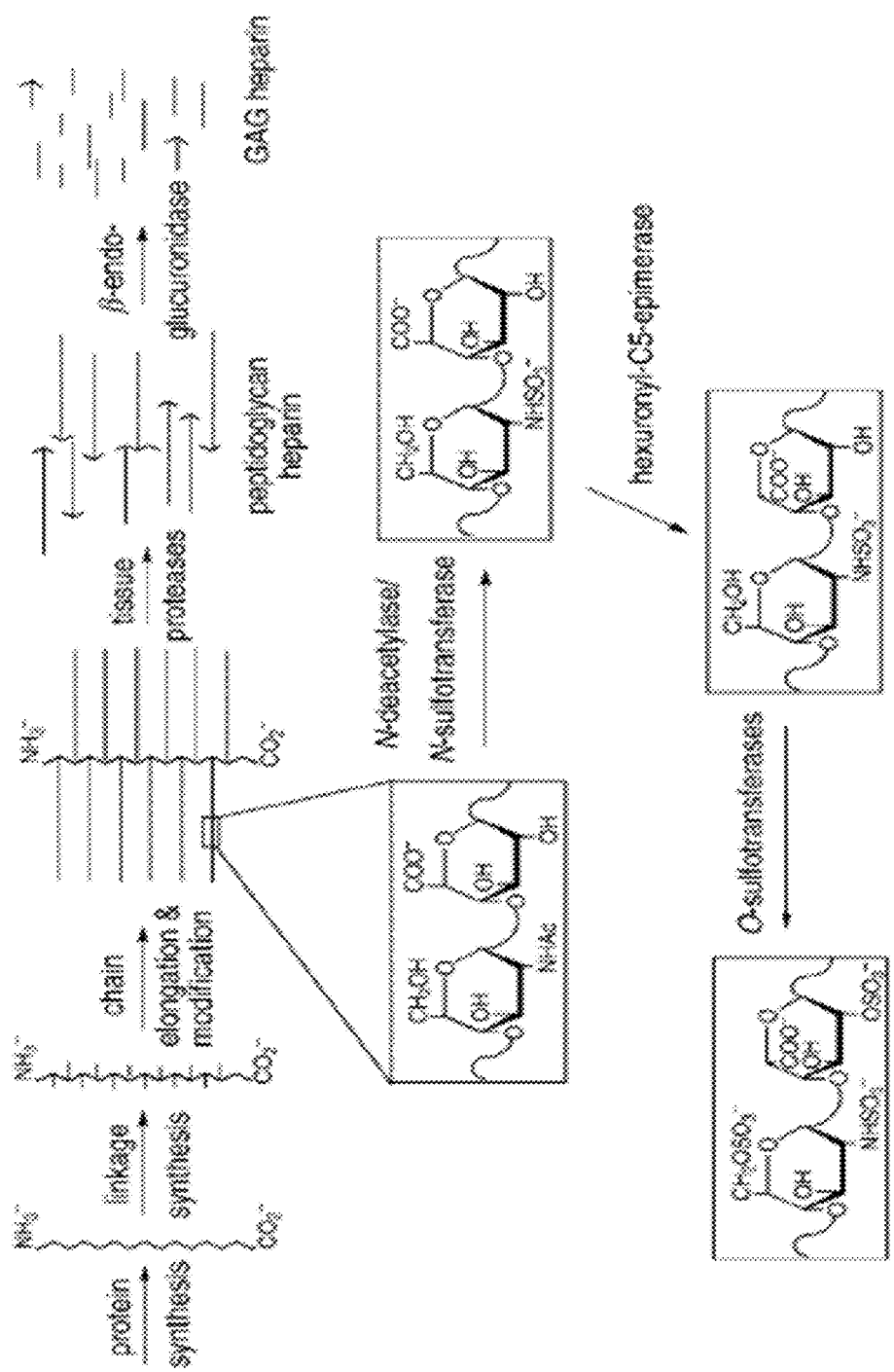
FIG. 1: Diagram of the biosynthetic process of heparin.

The following abbreviations and acronyms are used in the present specification:
NMR: Nuclear magnetic resonance
HSQC: Heteronuclear Single-Quantum Correlation
GAG: Glycosaminoglycan
UFH: Unfractionated heparin
LMWH: Low Molecular Weight Heparin
ULMWH: Ultra Low Molecular Weight Heparin
Da: Dalton
ΔU2S: 4,5-unsaturated 2-O sulfo uronic acid
ΔU: 4,5-unsaturated uronic acid
1,6-an.A: 2-N-sulfo-1,6-anhydroglucosamine
1,6-an.M: 2-N-sulfo-1,6-anhydro-mannosamine
TOCSY: TOtal Correlation SpectroscopY
TSP: Sodium salt of 3-(Trimethylsilyl)-Propionic-D4 acid
DMMA: Dimethylmalonic acid, derivative thereof, and or salt thereof
MHz: Megahertz
ppm: parts per million
δ: chemical shift
SW: Spectral width
TD: Time domain
T1: Longitudinal relaxation time
ANS: N-sulfoglucosamine
G: Glucuronic acid
ANS6S: N-sulfo-6-O-sulfoglucosamine I2S: 2-O-sulfoiduronic acid
I: Iduronic acid
ANS3S: N-sulfo-3-O-sulfoglucosamine
Gal: Galacturonic acid
Xyl: Xylose
ANAc: N-acetylglucosamine
A6S: 6-O-sulfoglucosamine
A6OH: Glucosamine
G2S: Sulfoglucuronic 2-0 acid
M: Mannosamine
MNS6S: N-sulfo-6-O-sulfomannosamine
Epox: Epoxide
αred: α anomer
βred: β anomer.

DETAILED DESCRIPTION OF THE INVENTION

As used herein, "monosaccharide residue present in heparin chains" refers to all monosaccharide residues or components that are typically present in LMWH/UFH/GAG chains. These residues are generally selected from the group consisting of 4,5-unsaturated 2-O sulfo uronic acid (ΔU2S), 4,5-unsaturated uronic acid (ΔU), 2-N-sulfo-1,6-anhydroglucosamine (1,6-an.A), 2-N-sulfo-1,6-anhydro-mannosamine (1,6-an.M), 2-N-sulfo-6-O-sulfoglucosamine (ANS6S), 2,5-anhydro mannitol, N-sulfoglucosamine, glucuronic acid, N-sulfo-6-O-sulfoglucosamine, 2-O-sulfoiduronic acid, iduronic acid, N-sulfo-3-O-sulfoglucosamine, N-sulfo-3,6-di-O-sulfoglucosamine, galacturonic acid, Xylose, N-acetylglucosamine and N-acetyl-6-O-sulfoglucosamine.

The invention provides a composition for NMR analysis of GAG's. The composition comprises at least one GAG (comprising plural saccharide residues having respective anomeric or target hydrogens) and at least one internal reference compound having a T1 for hydrogen of about the T1 for the anomeric or target hydrogen of at least one said plural saccharide residues. The composition can further comprise a deuterated solvent in which said at least one GAG is at least partially soluble or is fully soluble and in which said at least one internal reference compound is at least partially soluble or is fully soluble.

In some embodiments, the composition comprises at least one GAG, DMMA, and at least one deuterated solvent. The content of said components in the composition can be as described herein. The composition can be a sample composition.

A GAG comprises plural saccharide residues or at least two different saccharide residues. A saccharide residue will usually comprise an anomeric and/or target hydrogen atom(s). Anomeric or target hydrogens typically exhibit a T1 of about 1 sec or 1±0.2 sec or about 1 sec or less, of ≤about 1 sec. Anomeric hydrogens typically exhibit a chemical shift signal of about 4.5-6 ppm for $^1$H-NMR. At least hydrogen atom(s) of the internal reference standard will exhibit a singlet chemical shift reference signal outside the range of about 4.5-6 ppm, and the intensity of said reference signal will be concentration dependent. At least hydrogen atom(s) of the internal reference standard can exhibit a singlet chemical shift reference signal in the range of about 1.2 to about 1.4 ppm for $^1$H-NMR analysis and a singlet chemical shift signal within the range of about 26 ppm to about 27 ppm $^{13}$C-NMR. The concentration versus intensity typically exhibits an approximately linear relationship when said reference standard is present in the composition at least in the concentration range of about 0.2 mM to about 2.5 mM, and the linearity of said relationship can also exist outside said concentration range. The linearity can have a correlation coefficient of ≥0.90, ≥0.95, ≥0.98, or ≥0.99. 3-(trimethylsilyl)-priopionic-D4 acid (deuterated TSP) can be used as an internal chemical shift signal reference for 0 ppm in $^1$H-NMR. The concentration of total amount (concentration) of GAG, or at least one of its saccharide residues, is typically in the range of about 15 to about 700 mM, about 25 to about 600 mM, about 30 to about 500 mM, about 30 to about 400 mM, about 33 to about 333 mM, about 0.005 to about 1 mg/μL, about 0.01 mg/μL to about 0.5 mg/μL, or about 0.02 to about 0.2 mg/μL. At least one hydrogen of the internal reference standard will exhibit a T1 that approximates, is equal to, or is less than the T1 of the anomeric or target hydrogen of said saccharide residue(s), e.g. a T1 of about 1 sec or 1±0.2 sec or about 1 sec or less, of ≤about 1 sec. Combinations of two or more deuterated solvents can be used. An aqueous deuterated solvent can be used, e.g. D$_2$O or D$_2$O in combination with one or more deuterated organic solvents. The solvent or combination of solvents used will dissolve at least a portion of the GAG or will dissolve all of the GAG in the composition. The free acid or salt form of DMMA can be used.

The present invention provides a NMR method of determining the identity and relative content of individual saccharide residues forming a respective GAG. A NMR method of the invention is generally performed by: a) providing a sample composition comprising at least one GAG (comprising plural saccharide residues, each comprising at least one respective hydrogen and at least one respective carbon), at least one internal reference compound (as described herein for concentration standard), TSP (internal standard defining 0 ppm), and at least one deuterated solvent; b) conducting a 1D or 2D NMR analysis on said sample composition to obtain at least one reference chemical shift signal (for at least one hydrogen of said at least one internal reference and/or for at least one carbon of said at least one internal reference) and to obtain plural saccharide residue chemical shift signals (for said at least one respective hydrogens and/or for said at least one respective carbon of said respective said plural saccharide residue); c) normalizing said plural saccharide residue chemical shift signals relative to (with respect to) said at least one reference chemical shift signal(s); d) determining the relative percentage of individual ones of said plural saccharide residues in said at least one GAG; and e) correlating said plural saccharide residue chemical shift signals to known chemical shift signals for saccharide residue standards to determine the identity of individual ones of said plural saccharide residue. The above steps after b) need not be conducted sequentially, meaning steps c) through e) can be conducted in any order.

The relative percentage of individual saccharide residues in a GAG can be determined according to the following formula:

$$\% \text{ signal } X = \frac{\text{normalized value for signal } X}{\Sigma \text{ normalized value for all the signals}} \times 100.$$

wherein:
X is the target hydrogen.
normalized value for signal X is the chemical shift signal intensity for X after said signal has been normalized relative to the reference chemical shift signal, and Σ normalized value for all the signals is the sum total of all the normalized values.

A chemical shift signal pattern (or "NMR fingerprint"), as used herein, refers to the set of the signals corresponding to the peaks found in a determined NMR spectrum, whether one-dimensional $^1$H-NMR and/or two-dimensional $^1$H-$^{13}$C HSQC, or the absence thereof, in the relative proportions of its normalized integrals indicated by the parameter "relative proportion (%)". The chemical shift signal pattern can be a graphical spectrum (visual linear graph) or a numerical spectrum (group of values in a data set). The absence of particular chemical shift signals corresponds to the absence of respective saccharide residues and the presence of particular chemical shift signals corresponds to the presence of respective saccharide residues. The chemical shift signal pattern is used to identify, characterize, specify the saccharide composition of a corresponding GAG.

The method and composition of the invention can be practiced with any GAG known to date and any as yet unknown GAG, meaning any GAG discovered or first prepared after the date of the present invention.

Experimental Assays

The quantitative NMR assays have been performed using a Bruker AVIII-600 o AVIII-800 nuclear magnetic resonance (NMR) spectrometer. Reagents used were deuterium oxide (D$_2$O) 99.9%, sodium salt of 3-(Trimethylsilyl)-Propionic-D4 acid (TSP) and Dimethylmalonic acid (DMMA, standard for quantitative NMR, TraceCERT grade) as internal standard.

a) Equipment Conditions
   Frequency: $^1$H: 600/800 MHz, $^{13}$C: 150.9/201.2 MHz
   Temperature: 298 K
b) Acquisition Parameters (Quantitative $^1$H NMR)
   90° pulse: it is determined from a qualitative $^1$H spectrum
   Acquisition window: SW=10-12 ppm/TD=64-128 k
   Inter scans delay d1 must fulfil the condition d1+AQ≥20s
   No. of scans: 12
c) Acquisition Parameters (HSQC)
   90° pulse: it is determined from a qualitative $^1$H spectrum
   Acquisition window: SW2 ($^1$H)=6 ppm/TD(F2)=1 k
      SW1 ($^{13}$C)=120 ppm/TD(F1)=256-384
   Time between pulses d1=1.8-2 s
   No. of scans: 12
d) Processing Parameters ($^1$H)
   Processing window: SI=64-256K
   Window function: None
   Phase adjustment: manual
   Baseline adjustment: automatic (abs)
e) Processing Parameters (HSQC)
   Processing window: SI(F2)=2 k
   Processing function: QSINE, SSB=2
   Phase adjustment: manual
   Baseline adjustment: automatic
f) Preparation of the Sample: The Following Solutions were Prepared:
   Solution A (TSP) 1 mg/mL
   Solution B (D$_2$O-TSP) 0.002 mg/mL: 40 μL A (TSP)+ 19.96 mL D$_2$O, Total volume=20 mL
   Solution C (DMMA) 1.2 mg dimethylmalonic/mL of D$_2$O
   Test sample: 50 mg of product to study in 500 μL of the solution B (D$_2$O-TSP) and add 100 μL of solution C (DMMA) and place in 5 mm-diameter NMR tube.

The NMR tube containing the sample is introduced in the spectrometer. Then, the homogeneity of the magnetic field is adjusted and the harmony of the wave is optimized for the $^1$H and $^{13}$C nuclei. A qualitative $^1$H spectrum is then performed, with parameters similar to the aforementioned, except the following:
   Time between pulses d1=1-2 s; No. of scans: 1-4.
Then, the value of the 90° pulse is determined with automatic pulse program (TOPSPIN). Next, the quantitative $^1$H spectrum is performed, with the parameters indicated in the analytical method and the 90° pulse value (P1) previously determined. After the HSQC spectrum is obtained with the aforementioned parameters. The spectra obtained are then processed according to the aforementioned parameters, taking as chemical shift reference, the TSP-d4 signal at 0 ppm.

The dimethylmalonic acid reference chemical shift signals appear at the following approximate chemical shifts:
   $^1$H NMR: singlet that appears at about 1.2 to about 1.5 ppm, about 1.3 to about 1.5 ppm, about 1.4 to about 1.5 ppm, about 1.3 ppm, and about 1.4 ppm;
   HSQC: signal at about 1.2 to about 1.5 ppm, about 1.3 to about 1.5 ppm, about 1.4 to about 1.5 ppm, about 1.3 ppm, and about 1.4 ppm ($^1$H) and about 25 to about 27 ppm, about 26 ppm to about 27 ppm ($^{13}$C).

It should be understood that all chemical shift signals described herein are approximate and can vary slightly according to experimental conditions; however, said signals are obtained within the specified ranges when corresponding NMR analyses are conducted as described herein. Moreover, all ranges specified herein are inclusive of the range limits and all integer and fractional values therein especially as defined by the definition of the term "about" as used herein, and each said chemical shift is relative to TSP as the internal reference defining 0 ppm.

The parameters assessed to determine validation of the method for quantitative NMR have been the following:

Specificity

This aspect of the method determines the capacity of the analytical method for measuring and/or identifying, simultaneously or separately, the analytes of interest unequivocally in presence of other chemical substances that may be present in the sample.

The data obtained in the $^1$H NMR analyses were as follows:

| Sample | Composition | Chemical shift, ppm |
| --- | --- | --- |
| I, solvent | D$_2$O | 4.79 |
| II, chemical shift reference | D$_2$O-TSP | 0.00 |
| III, internal standard | D$_2$O-DMMA | 1.42 |
| IV, GAG sample | D$_2$O-TSP-DMMA-GAG | 1.8-8.0 |

The data obtained in the $^1$H $^{13}$C-HSQC analyses were as follows:

| Sample | Composition | Chemical shift $^1$H, ppm | Chemical shift $^{13}$C, ppm |
| --- | --- | --- | --- |
| III, internal standard | D$_2$O-DMMA | 1.42 | 25.42 |
| IV, sample: GAG | D$_2$O-TSP-DMMA-GAG | 1.8-8.0 | 24-112 |

Figure 2:
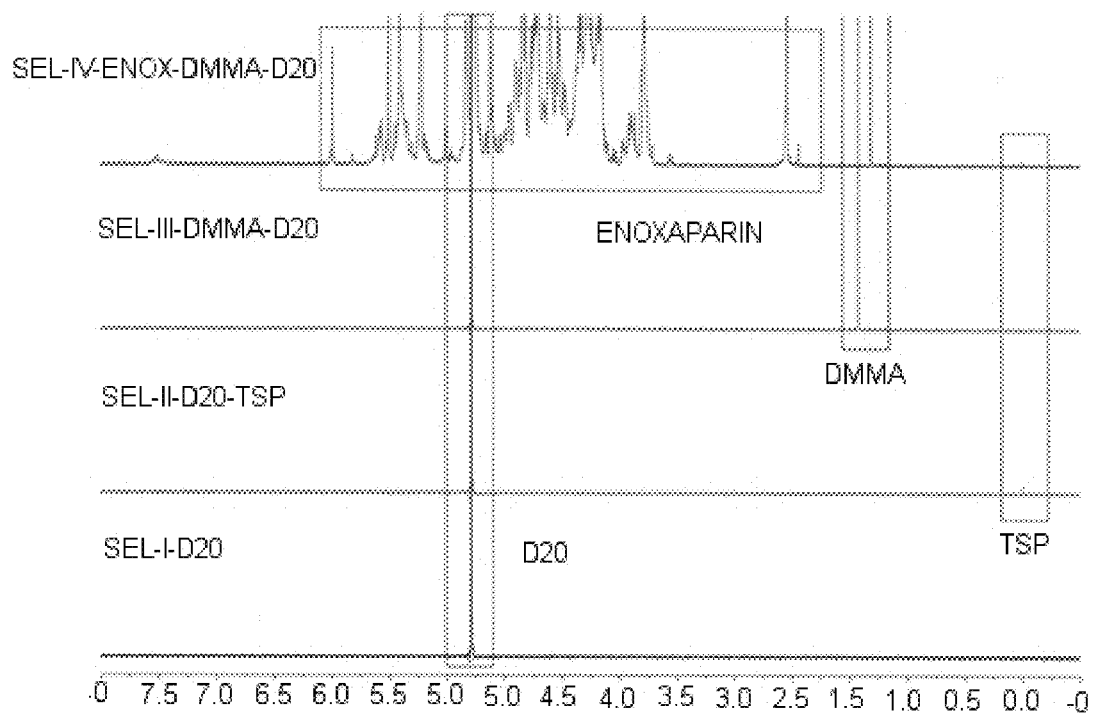
FIG. 2: Specificity. $^1$H-NMR spectra: a) SEL-I-D2O: spectrum of D$_2$O solvent; b) SEL-II-D2O-TSP: spectrum of combination of D$_2$O solvent and TSP; c) SEL-III-DMMA-D2O: spectrum of combination of D$_2$O solvent and DMMA; d) SEL-IV-ENOX-DMMA-D2O: spectrum of combination of enoxaparin, D$_2$O solvent and DMMA.
Figure 3:
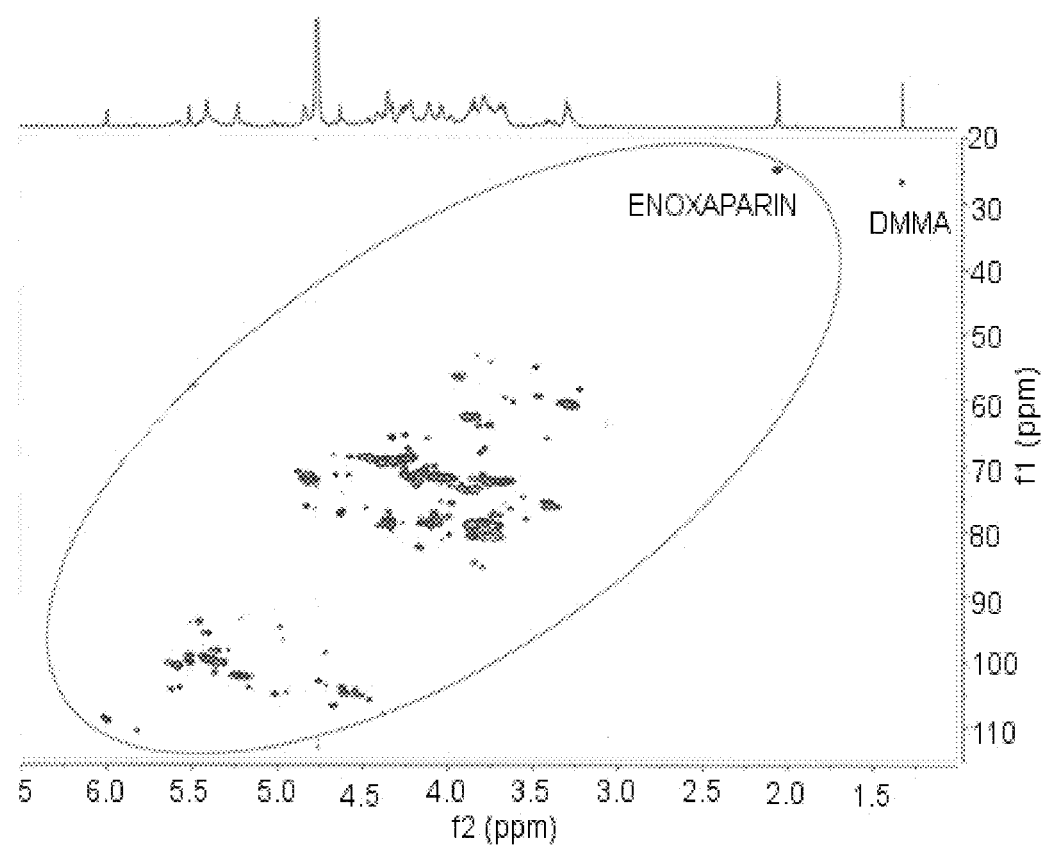
FIG. 3: Specificity. $^1$H-$^{13}$C HSQC spectra of SEL-IV-ENOX-DMMA-D2O. The spectrum was obtained under the following conditions: Temperature: 298.0 K; number of scans: 12; receiver gain: 2050.0; relaxation delay: 1.8; pulse width: 11.11; acquisition time: 0.1068 s; JCH: 170; spectrometer frequency: 800.13, 201.49; spectral width (ppm): 4795.4, 24154.6; lowest frequency: 447.9, 575.7.

We found no interference between chemical shift signal for the DMMA and GAG in the $^1$H NMR or $^1$H $^{13}$C-HSQC spectra (FIGS. 2 and 3). The data demonstrate that the method is capable of discriminating, without interference or undue chemical shift overlap, the chemical shift signals of the GAG from those of other products present in the sample such as the solvent (deuterium oxide, D$_2$O), the internal standard (DMMA) and the chemical shift reference (TSP-d4).

Limit of Quantification and Linearity

Under these parameters, on the one hand, the minimum quantity of analyte that may be suitably quantified precisely and accurately is determined and, on the other hand, the capacity of the method to obtain results directly (by means of mathematical transformations) proportional to the concentration of the analyte in the sample, within an established interval.

To assess the limit of quantification and the linearity (of chemical shift signal intensity dependence upon concentration of sample) of the integrals (for said chemical shift signal) of the DMMA, corresponding chemical shift signals were quantified. Solution comprising enoxaparin sodium (fixed concentration) and DMMA (seven different concentrations of DMMA) were prepared as follows:

0.2 mM of DMMA: 13.5% of the working concentration
0.3 Mm of DMMA: 20.3% of the working concentration
0.76 mM of DMMA: 50% of the working concentration
1.2 mM of DMMA: 80.1% of the working concentration
1.5 mM of DMMA: 100% of the working concentration
1.8 mM of DMMA: 120% of the working concentration
2.27 mM of DMMA: 150.2% of the working concentration.

Figure 4:
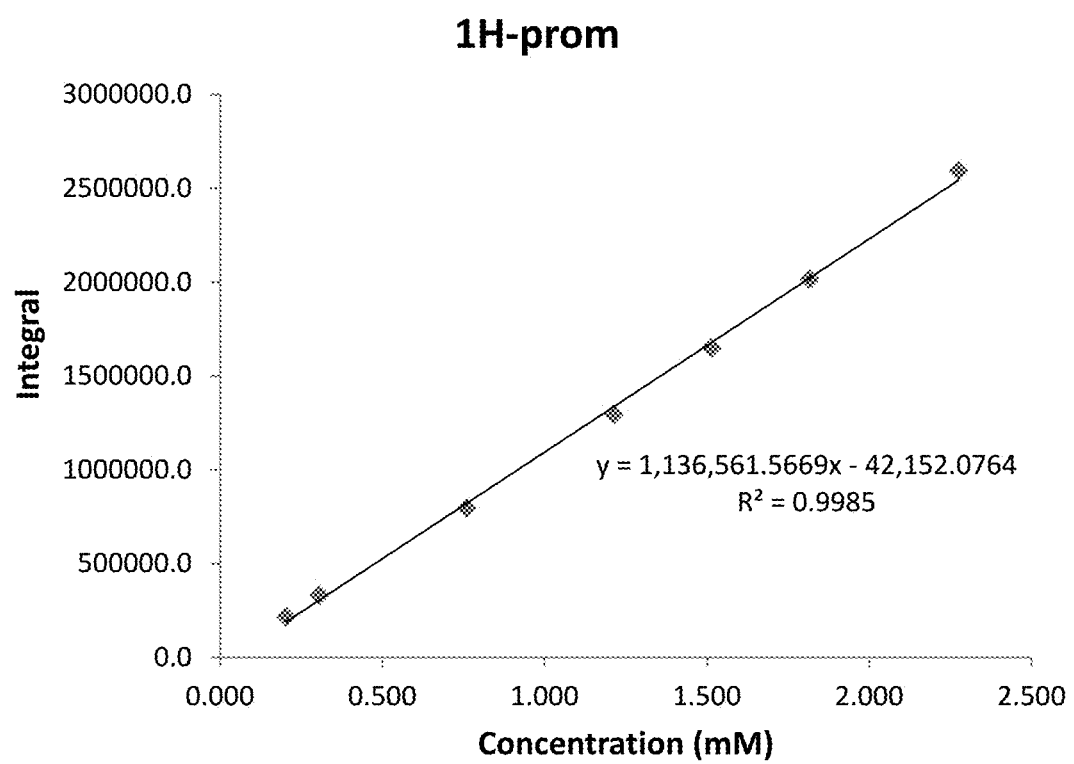
FIG. 4: $^1$H-NMR linearity. Graph depicting the linearity of concentration (mM) of DMMA (variable X) versus the integral (variable Y) of its $^1$H chemical shift signal. Under the conditions of the assay employed, the linearity is defined by the following equation: y=1,136,561.5669x−42,152.0764 with an R$^2$ value of 0.9985.
Figure 5:
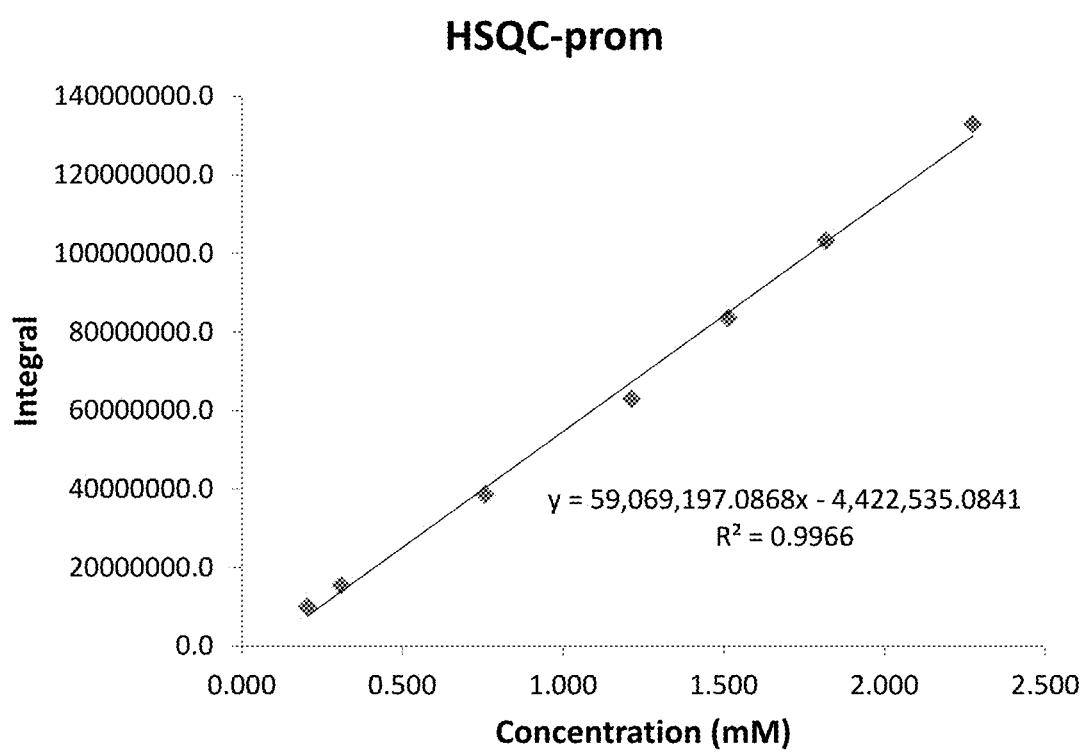
FIG. 5: $^1$H-$^{13}$C HSQC linearity. Graph depicting the linearity of concentration (mM) of DMMA (variable X) versus the integral (variable Y) of its $^1$H chemical shift signal. Under the conditions of the assay employed, the linearity is defined by the following equation: y=59,069,197.0868x−4,422,535.0841, with an R$^2$ value of 0.9966
Figure 6:
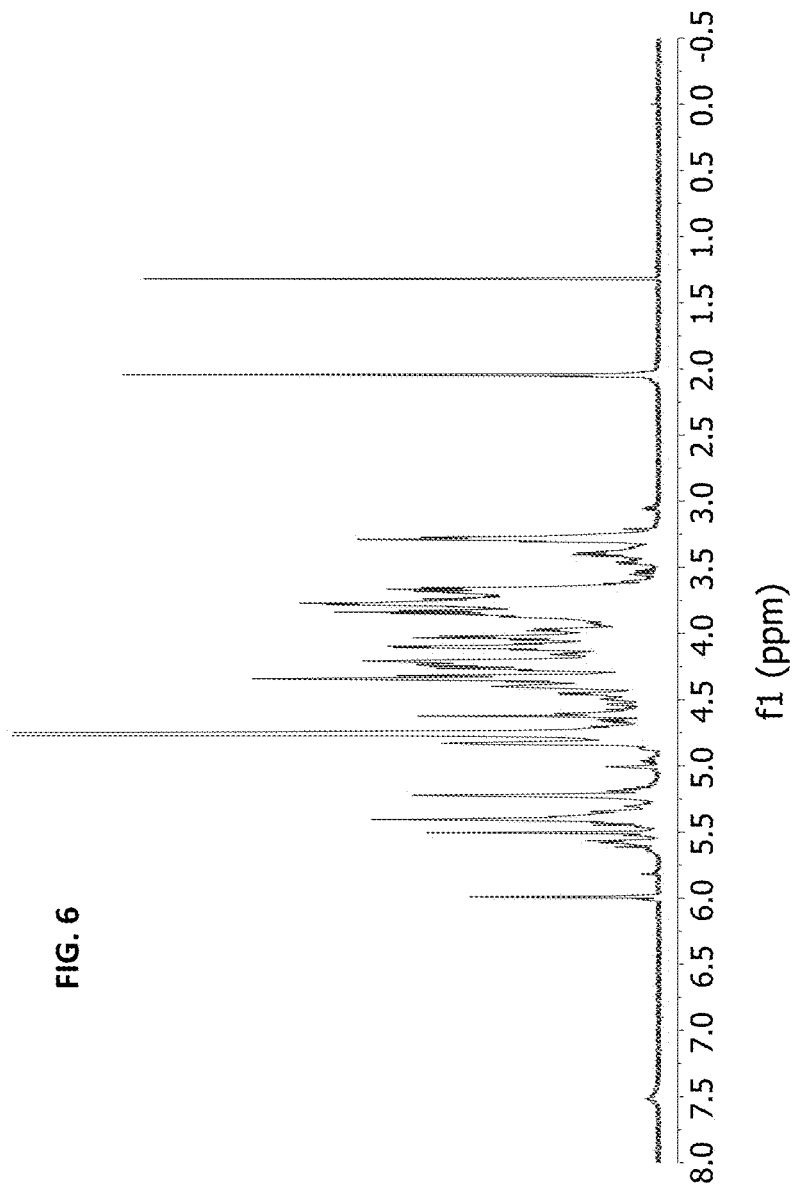
FIG. 6: $^1$H-NMR spectrum of enoxaparin sodium. The spectrum was obtained under the following conditions: Temperature: 298.0 K; number of scans: 12; receiver gain: 2.0; relaxation delay: 13.5; pulse width: 10.69; acquisition time: 6.8157 s; JCH: 1; spectrometer frequency: 800.13; spectral width (ppm): 12.0.
Figure 7:
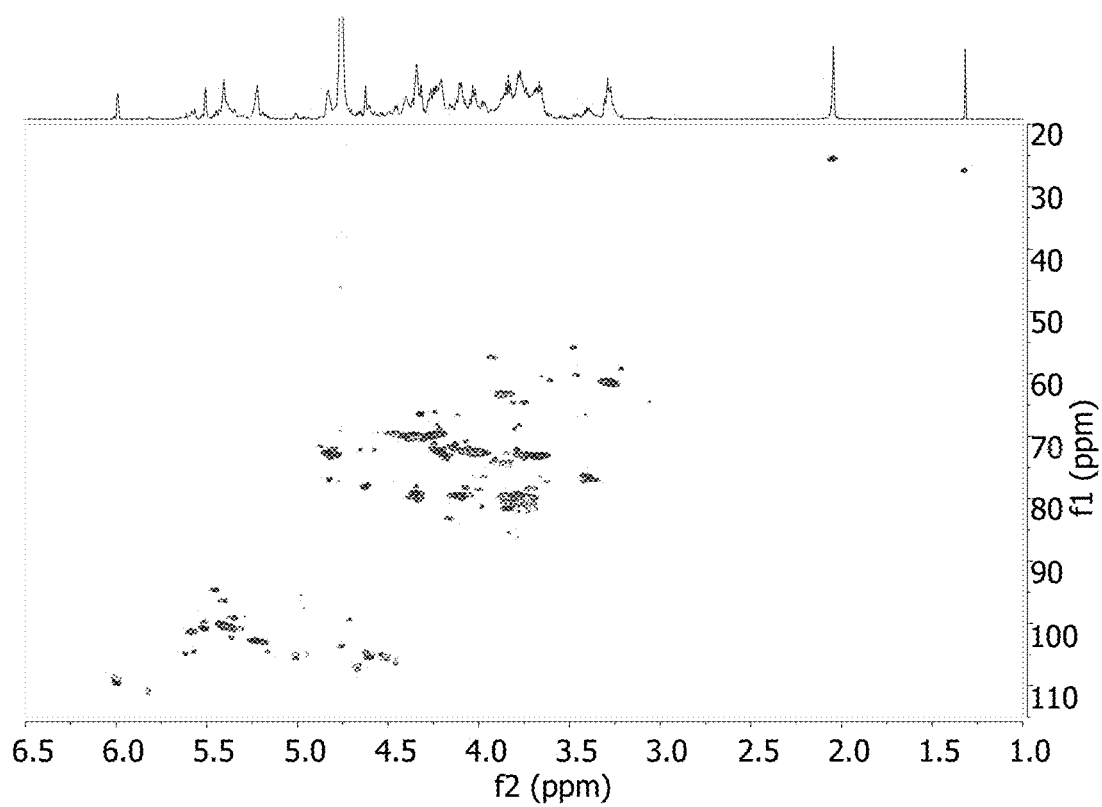
FIG. 7: $^1$H-$^{13}$C HSQC spectrum of enoxaparin sodium. The spectrum was obtained under the following conditions: Temperature: 298.0 K; number of scans: 12; receiver gain: 2050.0; relaxation delay: 1.8; pulse width: 10.69; acquisition time: 0.1068 s; JCH: 170; spectrometer frequency: 800.13, 201.19; spectral width: 4795.4, 24154.6; lowest frequency: 447.9, 575.7.

The acceptance criteria established to fulfil this linearity criterion is that in the line obtained the correlation coefficient for both experiments is ≥0.99. In FIGS. 4 and 5 depicts a graph of the DMMA signal integral values vs. DMMA concentration (mM), for the $^1$H NMR and $^1$H $^{13}$C-HSQC spectra. The acceptance criterion is easily fulfilled both for one and the other.

The lower limit of quantification for a DMMA is a concentration of about 0.20 mM or ≥20 mM. Thus, the signals of the samples studied with intensity less than the intensity of the DMMA signal corresponding to this concentration, cannot be suitably quantified and, therefore, they cannot be taken to determine the relative proportion of the residues present in the molecule. This means that the GAG, or at least one of its corresponding saccharide residues, should be present in the sample composition at a concentration of at least about 0.2 mM or ≥20 mM.

Accuracy

This aspect of the methods determines the proximity between the value which is accepted conventionally as true or reference value and the experimental value found. To calculate the experimental value of the concentration of the samples in analyte solution, you correlate the signal integral of the analyte to the signal integral of the DMMA, for example the equation defining the linearity (described above) of signal intensity versus concentration for DMMA can be used to determine the corresponding concentration of analyte in the sample.

The accuracy is expressed as recovery percentage in the value of a known quantity of internal standard:

$$\text{Recovery percentage}(R) = \frac{Xm}{\mu} \times 100$$

Where: Xm is mean value found, and p is the value accepted as true.

The acceptance criteria established is that the recovery values are between 70.0-130.0% for the concentration corresponding to the concentration limit and 80.0-120.0% for the other levels.

The data obtained for the $^1$H NMR and HSQC experiments were the following:

a) $^1$H NMR

| Concentration, mM | Conc. Calculated, mM | Recovery, $^1$H NMR |
|---|---|---|
| 0.204 | 0.228 | 111.77 |
| 0.307 | 0.330 | 107.31 |
| 0.758 | 0.737 | 97.26 |
| 1.212 | 1.175 | 96.90 |
| 1.514 | 1.488 | 98.29 |
| 1.817 | 1.810 | 99.65 |
| 2.274 | 2.318 | 101.94 | b) HSQC

| Concentration, mM | Conc. Calculated, mM | Recovery, HSQC |
|---|---|---|
| 0.204 | 0.243 | 119.17 |
| 0.307 | 0.337 | 109.81 |
| 0.758 | 0.727 | 95.96 |
| 1.212 | 1.140 | 94.03 |
| 1.514 | 1.488 | 98.29 |
| 1.817 | 1.823 | 100.32 |
| 2.274 | 2.328 | 102.37 |

Both the $^1$H NMR and HSQC methods provide accuracy in compliance with the acceptance criteria for the accuracy parameters for those signals corresponding to the sample, with intensity higher than that of the limit of quantification.

Precision—Repeatability—Reproducibility

The intra-sample variability of the method is studied by performing a series of analyses on the same sample in the same operating conditions in a same laboratory and in a short period of time.

To do this, three consecutive analyses were performed for each concentration. The repeatability of a method is expressed as the coefficient of variation (CV) of a series of measurements and is mathematically calculated as follows:

$$CV(\%) = \frac{s}{X} \times 100,$$

where: s is standard deviation, and X is arithmetic means of the results.

The acceptance criterion established to fulfill these accuracy criteria is a coefficient of variation for all levels of ≤7%.

The data obtained for both experiments was the following:

| Concentration, mM | CV, % $^1$H NMR | CV, % HSQC |
|---|---|---|
| 0.204 | 5.55 | 3.40 |
| 0.307 | 0.09 | 2.29 |
| 0.758 | 1.62 | 1.45 |
| 1.212 | 1.74 | 2.52 |
| 1.514 | 1.41 | 1.01 |
| 1.817 | 2.16 | 3.99 |
| 2.274 | 2.30 | 2.73 |

Both the $^1$H NMR and HSQC methods provide reproducibility in compliance with the acceptance criterion for the accuracy parameters for those signals corresponding to the sample, with intensity higher than that of the limit of quantification.

EXAMPLES

The following specific examples provided below serve to illustrate the nature of the present invention. These examples are included only for illustration purposes and are not to be deemed to limit the invention to just said exemplary embodiments. The invention is defined by the claims, drawings, abstract and entire specification.

Example 1

$^1$H NMR of Enoxaparin Sodium

Enoxaparin sodium (50 mg) are dissolved in 500 μL of a D$_2$O-TSP (solution B) solution. Then 100 μL of DMMA solution (solution C) are added. The resulting solution is introduced in a 5 mm diameter tube.

The resulting DMMA concentration in the solution is 1.5 mM. The experiments are performed on a Bruker AVIII-800 nuclear magnetic resonance spectrometer. The main signals identified are as follows:

| Signal | Chemical shift, ppm |
|---|---|
| H4 ΔU2S | 5.992 |
| H4 ΔU2 | 5.825 |
| H1 1,6-AnA | 5.616 |
| H1 ANS(-G) | 5.585 |
| H1 1,6-AnM | 5.569 |
| H1 ΔU2S | 5.509 |
| H1 ANS6S | 5.405 |
| H1 I2S | 5.228 |
| H1 I | 5.012 |
| H5 I2S | 4.836 |
| H1 G | 4.628 |
| H6 ANS6S | 4.344 |
| H6' ANS6S | 4.210 |
| H3 ANS | 3.670 |
| H2 ANS3S | 3.395 |
| H2 ANS | 3.293 |
| NAc | 2.047 |
| DMMA | 1.320 |
| TSP | 0.069 |

Once the values of the integrals of the signals both of DMMA and the rest of the residues have been obtained, the normalized values are obtained of said residues dividing the value of its integrals by the value of the integral corresponding to the DMMA signal. This normalization can be performed, because the concentration of the internal standard is kept constant with respect to the saccharide residue concentration for all experiments, thus avoiding the inter-experimental variability that may arise in the analysis of a series of several product batches.

Once the normalized values of the residues have been obtained, the relative percentage of each one of them is calculated in accordance with the following formula:

$$\% \text{ signal } X = \frac{\text{normalized value signal } X}{\sum \text{normalized value all the signals}} \times 100$$

To clarify the steps performed, the results obtained are shown for a series of four samples M1, M2, M3 and M4 of enoxaparin sodium. The following integral values of each one of the chemical shift signals selected were obtained.

| | Integral | | | |
|---|---|---|---|---|
| Signal | M 1 | M 2 | M 3 | M 4 |
| H4 ΔU2S | 2767732.83 | 2988384.02 | 3075705.31 | 2332763.55 |
| H4 ΔU | 114294.94 | 135658.19 | 143037.09 | 94201.86 |
| H1 1,6-an.A | 404060.73 | 472871.53 | 509930.86 | 351978.17 |
| H1 1,6-an.M | 2535227.20 | 2700027.94 | 2844751.53 | 2160178.72 |
| H1 ΔU2S | 3541377.06 | 3818336.16 | 3951288.34 | 2999870.34 |
| H1 ANS6S | 10350026.69 | 10716882.48 | 10780945.33 | 8442504.14 |
| H1 I2S | 8922576.12 | 9200191.38 | 9486264.66 | 7346708.47 |
| H5 I2S | 8924825.12 | 9540022.53 | 10041127.64 | 7751650.03 |
| H2 ANS | 16351247.22 | 16802874.61 | 17051664.14 | 13189968.22 |
| NAc | 8054931.36 | 7973188.48 | 8124533.56 | 6388424.34 |
| DMMA | 1464255.27 | 1415020.17 | 1485242.95 | 1279612.94 |

To obtain the normalized values of the integrals of the chemical shift signals, their respective integrals are divided by the integral of the DMMA (present at a known or determined concentration):

| | Normalized integral | | | |
|---|---|---|---|---|
| Signal | M 1 | M 2 | M 3 | M 4 |
| H4 ΔU2S | 1.890 | 2.112 | 2.071 | 1.823 |
| H4 ΔU | 0.078 | 0.096 | 0.096 | 0.074 |
| H1 1,6-an.A | 0.276 | 0.334 | 0.343 | 0.275 |
| H1 1,6-an.M | 1.731 | 1.908 | 1.915 | 1.688 |
| H1 ΔU2S | 2.419 | 2.698 | 2.660 | 2.344 |
| H1 ANS6S | 7.068 | 7.574 | 7.259 | 6.598 |
| H1 I2S | 6.094 | 6.503 | 6.387 | 5.741 |
| H5 I2S | 6.095 | 6.742 | 6.761 | 6.058 |
| H2 ANS | 11.167 | 11.875 | 11.481 | 10.308 |
| NAc | 5.501 | 5.635 | 5.470 | 4.992 |
| DMMA | 1.000 | 1.000 | 1.000 | 1.000 |

From these normalized values, the relative proportion of each one of the chemical shift signals is calculated with respect to the sum of all the normalized chemical shift signals.

| | Relative proportion, % | | | |
|---|---|---|---|---|
| Signal | M 1 | M 2 | M 3 | M 4 |
| H4 ΔU2S | 4.47 | 4.64 | 4.66 | 4.57 |
| H4 ΔU | 0.18 | 0.21 | 0.22 | 0.18 |
| H1 1,6-an.A | 0.65 | 0.73 | 0.77 | 0.69 |
| H1 1,6-an.M | 4.09 | 4.20 | 4.31 | 4.23 |
| H1 ΔU2S | 5.72 | 5.93 | 5.99 | 5.88 |
| H1 ANS6S | 16.70 | 16.65 | 16.33 | 16.54 |
| H1 I2S | 14.40 | 14.30 | 14.37 | 14.39 |
| H5 I2S | 14.40 | 14.83 | 15.21 | 15.18 |
| H2 ANS | 26.39 | 26.11 | 25.83 | 25.83 |
| NAc | 13.00 | 12.39 | 12.31 | 12.51 |

The quantification of the characteristic and well-differentiated signals of enoxaparin sodium (generally those corresponding to the anomeric or target protons, H1) are shown in the following table with the observed relative proportion values:

| Signal | Chemical shift, ppm | Relative proportion, % |
|---|---|---|
| H4 ΔU2S | 5.99 | 4.3-4.7 |
| H4 ΔU | 5.82 | 0.2 |
| H1 1,6-an.A | 5.62 | 0.7-0.9 |
| H1 1,6-an.M | 5.57 | 4.1-4.4 |
| H1 ΔU2S | 5.51 | 5.7-6.0 |
| H1 ANS6S | 5.40 | 16.1-16.7 |

-continued

| Signal | Chemical shift, ppm | Relative proportion, % |
|---|---|---|
| H1 I2S | 5.23 | 13.1-14.4 |
| H5 I2S | 4.84 | 14.3-16.3 |
| H2 ANS | 3.29 | 24.3-26.6 |
| NAc | 2.05 | 12.0-15.3 |

The set of the signals corresponding to the peaks found in a determined NMR spectrum, whether one-dimensional $^1$H-NMR and/or two-dimensional $^1$H-$^{13}$C HSQC, or the absence thereof, in the relative proportions of its normalized integrals indicated by the parameter "relative proportion (%)" is what in the present specification is called "signal pattern" or simply "pattern".

Example 2

The same solution used in Example 1 is used to perform the study by 1H-$^{13}$C HSQC. The main signals identified are as follows:

| Signal ppm | δ $^{13}$C, ppm | δ $^1$H, ppm |
|---|---|---|
| C4-H4 ΔU | 110.71 | 5.82 |
| C4-H4 ΔU2S | 108.97 | 5.99 |
| C1-H1 G // Gal | 106.62 | 4.66 |
| C1-H1 Xyl | 105.79 | 4.45 |
| C1-H1 G(-ANAc) | 105.13 | 4.50 |
| C1-H1 I(-A6S) | 104.94 | 5.01 |
| C1-H1 G(-ANS) | 104.77 | 4.60 |
| C1-H1 I(-A6OH) | 104.67 | 4.94 |
| C1-H1 Gal | 104.30 | 4.54 |
| C1-H1 1,6-an.A | 104.22 | 5.61 |
| C1-H1 G(-ANS3S) | 103.91 | 4.61 |
| C1-H1 1,6-an.M | 103.91 | 5.57 |
| C1-H1 ΔU | 103.88 | 5.16 |
| C1-H1 G2S | 102.99 | 4.75 |
| C1-H1_I2S | 102.09 | 5.22 |
| C1-H1 I2S(-1,6-an.M) | 101.59 | 5.36 |
| C1-H1 ANS(-G) | 100.50 | 5.58 |
| C1-H1 ANAc | 100.23 | 5.31 |
| C1-H1 ΔU2S | 100.18 | 5.51 |
| C1-H1 ANS(-I2S) | 99.78 | 5.40 |
| C1-H1 ANS6S | 99.43 | 5.43 |
| C1-H1 ANS,3S | 99.06 | 5.51 |
| C1-H1 ANS βred | 98.73 | 4.71 |
| C1-H1 ANS(-I) | 98.42 | 5.34 |
| C1-H1 M αred | 95.74 | 5.39 |
| C1-H1 I2S αred | 95.70 | 5.42 |
| C1-H1 I2S βred | 94.76 | 4.97 |
| C1-H1 ANS αred//ANS6S red | 93.97 | 5.45 |
| C3-H3 Gal | 85.45 | 3.78 |
| C3-H3 Gal | 84.85 | 3.83 |
| C4-H4 ANS6S(-G)//ANS6S red | 80.94 | 3.84 |
| C2-H2 I2S | 78.53 | 4.34 |
| C3-H3 Xyl | 77.82 | 3.72 |
| C2-H2 ΔU2S | 77.42 | 4.62 |
| C2-H2 G(-AN6S) | 75.70 | 3.40 |
| C3-H3 ANS6S (-G) | 72.47 | 3.66 |
| C3-H3 ANS6S red | 72.29 | 3.77 |
| C5-H5 I2S | 72.01 | 4.83 |
| C3-H3 I2S | 71.87 | 4.21 |
| C5-H5 ANS6S(-G) | 71.72 | 4.09 |
| C5-H5 MNS6S red | 70.98 | 4.15 |
| C5-H5 ANS6S red | 70.64 | 4.12 |
| C6-H6 1,6-an.A//1,6-an.M | 67.53 | 3.77 |
| C5-H5 Xyl | 65.89 | 4.12 |
| C5-H5 Xyl | 65.86 | 3.40 |
| C3-H3 ΔU2S | 65.75 | 4.32 |
| C6-H6 Gal | 63.90 | 3.74 |
| C2-H2 ANS6S red//ANS(-I2S) | 60.82 | 3.28 |
| C2-H2 ANS6S(-G) | 60.52 | 3.29 |
| C2-H2 MNS6S red | 60.38 | 3.60 |
| C2-H2 1,6-an.A | 58.50 | 3.21 |
| C2-H2 ANAc | 56.68 | 3.92 |
| C2-H2 1,6-an.M | 55.09 | 3.47 |
| DMMA | 26.73 | 1.32 |
| NAc | 24.87 | 2.05 |

These signals are then correlated with monosaccharide components of the molecule, so that their quantification provides a chemical shift signal pattern representative of the monosaccharide content of the GAG.

The integral for each one of these $^{13}$C chemical shift signals was normalized from the value set for the integral of the reference $^{13}$C chemical shift signal of DMMA, using the same process (calculations) described for the $^1$H NMR experiments. The quantification of the characteristic signals of enoxaparin sodium is shown in the following table:

| Signal | Relative proportion, % |
|---|---|
| C1-H1 ANS-I2S | 25.6-26.9 |
| C1-H1 ANS-I | 2.6-3.0 |
| C1-H1 ANS-G | 5.1-5.5 |
| C1-H1 ANS.3S | 1.5-1.7 |
| C1-H1 ANAc | 2.7-3.5 |
| C1-H1 ANAc-αred | <LC |
| C1-H1 ANS-red | 3.8-4.9 |
| C1-H1 1,6-an.A | 1.2-1.5 |
| C1-H1 1,6-an.M | 1.6-1.9 |
| C1-H1 MNS-αred | 1.0-1.3 |
| C1-H1 I2S | 24.5-27.5 |
| C1-H1 I-A6S | 2.4-2.7 |
| C1-H1 I-A6OH | 0.3-0.4 |
| C1-H1 G-ANS.3S | 1.4-1.6 |
| C1-H1 G-ANS | 4.2-4.4 |
| C1-H1 G-ANAc | 1.9-2.6 |
| C1-H1 G2S | 1.1-1.6 |
| C1-H1 ΔU2S | 11.5-12.4 |
| C1-H1 ΔU | 0.3-0.5 |
| C1-H1 I2S-red | 1.0-1.4 |
| C5-H5 Gal-A | <LC-0.5 |
| Epox | <LC-0.4 |

These experiments demonstrate that, using the experimental conditions described above, it is possible to obtain an analysis method by nuclear magnetic resonance ($^1$H-NMR and $^1$H-$^{13}$C HSQC) of glycosaminoglycans in general, and of heparins and low molecular weight heparins and their derivatives in particular, which allows their quantitative analysis.

Example 3

Study by $^1$H NMR of Bemiparin Sodium

The main $^1$H chemical shift signals identified were as follows: Signal Chemical Signal Chemical shift, ppm shift, ppm

| Signal | Chemical shift, ppm |
|---|---|
| H4 ΔU2S | 5.992 |
| H4 ΔU | 5.825 |
| H1 1,6-AnA | 5.616 |
| H1 ANS(-G) | 5.585 |
| H1 1,6-AnM | 5.569 |
| H1 ΔU2S | 5.509 |
| H1 ANS6S | 5.405 |
| H1 I2S | 5.228 |
| H1 I | 5.012 |
| H5 I2S | 4.836 |
| H1 G | 4.628 |
| H6 ANS6S | 4.344 |
| H6' ANS6S | 4.210 |
| H3 ANS | 3.670 |
| H2 ANS3S | 3.395 |
| H2 ANS | 3.293 |
| NAc | 2.047 |
| DMMA | 1.320 |
| TSP | 0.069 |

The quantification of the characteristic and well-differentiated signals of bemiparin sodium (generally those corresponding to the anomeric or target protons, H1) are shown in the following table, with the values of relative proportions observed for a series of six samples.

| Signal | Chemical shift, ppm | Relative proportion, % |
|---|---|---|
| H4 ΔU2S | 5.99 | 3.7-5.7 |
| H4 ΔU | 5.82 | 0.2-2.5 |
| H1 1,6-an.A | 5.62 | 0.5-2.5 |
| H1 1,6-an.M | 5.57 | 2.5-6.0 |
| H1 ΔU2S | 5.51 | 7.0-10.7 |
| H1 ANS6S | 5.40 | 19.0-21.3 |
| H1 I2S | 5.23 | 13.8-18.5 |
| H2 ANS | 3.29 | 18.7-26.3 |
| NAc | 2.05 | 9.4-14.4 |

Example 4

The same solution used in example 3, is used to perform the study by H-$^{13}$C HSQC. The main $^1$H and $^{13}$C chemical shift signals identified were as follows:

| Signal ppm | δ $^{13}$C, ppm | δ $^1$H, ppm |
|---|---|---|
| C4-H4 ΔU | 110.71 | 5.82 |
| C4-H4 ΔU2S | 108.97 | 5.99 |
| C1-H1 G // Gal | 106.62 | 4.66 |
| C1-H1 Xyl | 105.79 | 4.45 |
| C1-H1 G(-ANAc) | 105.13 | 4.50 |
| C1-H1 I(-A6S) | 104.94 | 5.01 |
| C1-H1 G(-ANS) | 104.77 | 4.60 |
| C1-H1 I(-A6OH) | 104.67 | 4.94 |
| C1-H1 Gal | 104.30 | 4.54 |
| C1-H1 1.6-an.A | 104.22 | 5.61 |
| C1-H1 G(-ANS3S) | 103.91 | 4.61 |
| C1-H1 1.6-an.M | 103.91 | 5.57 |
| C1-H1 ΔU | 103.88 | 5.16 |
| C1-H1 G2S | 102.99 | 4.75 |
| C1-H1_I2S | 102.09 | 5.22 |
| C1-H1 I2S(-1,6-an.M) | 101.59 | 5.36 |
| C1-H1 ANS(-G) | 100.50 | 5.58 |
| C1-H1 ANAc | 100.23 | 5.31 |
| C1-H1 ΔU2S | 100.18 | 5.51 |
| C1-H1 ANS(-I2S) | 99.78 | 5.40 |
| C1-H1 ANS6S | 99.43 | 5.43 |
| C1-H1 ANS,3S | 99.06 | 5.51 |
| C1-H1 ANS βred | 98.73 | 4.71 |
| C1-H1 ANS(-I) | 98.42 | 5.34 |
| C1-H1 M αred | 95.74 | 5.39 |
| C1-H1 I2S αred | 95.70 | 5.42 |
| C1-H1 I2S βred | 94.76 | 4.97 |
| C1-H1 ANS αred// ANS6S red | 93.97 | 5.45 |
| C3-H3 Gal | 85.45 | 3.78 |
| C3-H3 Gal | 84.85 | 3.83 |
| C4-H4 ANS6S(-G)// ANS6S red | 80.94 | 3.84 |
| C2-H2 I2S | 78.53 | 4.34 |
| C3-H3 Xyl | 77.82 | 3.72 |
| C2-H2 ΔU2S | 77.42 | 4.62 |
| C2-H2 G(-AN6S) | 75.70 | 3.40 |
| C3-H3 ANS6S (-G) | 72.47 | 3.66 |
| C3-H3 ANS6S red | 72.29 | 3.77 |
| C5-H5 I2S | 72.01 | 4.83 |
| C3-H3 I2S | 71.87 | 4.21 |
| C5-H5 ANS6S(-G) | 71.72 | 4.09 |
| C5-H5 MNS6S red | 70.98 | 4.15 |
| C5-H5 ANS6S red | 70.64 | 4.12 |
| C6-H6 1,6-an.A// 1,6-an.M | 67.53 | 3.77 |
| C5-H5 Xyl | 65.89 | 4.12 |
| C5-H5 Xyl | 65.86 | 3.40 |
| C3-H3 ΔU2S | 65.75 | 4.32 |
| C6-H6 Gal | 63.90 | 3.74 |
| C2-H2 ANS6S red// ANS(-I2S) | 60.82 | 3.28 |
| C2-H2 ANS6S(-G) | 60.52 | 3.29 |
| C2-H2 MNS6S red | 60.38 | 3.60 |
| C2-H2 1.6-an.A | 58.50 | 3.21 |
| C2-H2 ANAc | 56.68 | 3.92 |
| C2-H2 1.6-an.M | 55.09 | 3.47 |
| DMMA | 26.73 | 1.32 |
| NAc | 24.87 | 2.05 |

The signals were correlated with particular saccharides (based upon comparison of said signals to those of reference monosaccharides), and after normalization of the respective integrals of said signals with respect to the integral of the DMMA reference, and after determining the relative percentage of the individual signals, a quantitative chemical shift pattern for the GAG was obtained.

Specifically, the integral of each one of the above signals was normalized with respect to the integral of DMMA, using the same procedure explained for the experiments $^1$H MMR. Accordingly, the quantitative relative content (proportion) of each saccharide in bemiparin sodium is detailed in the following table.

| Signal | Relative proportion, % |
|---|---|
| C1-H1 ANS-I2S | 26.5-30.6 |
| C1-H1 ANS-I | 1.7-5.3 |
| C1-H1 ANS-G | 2.1-3.8 |
| C1-H1 ANS.3S | 0.6-2.5 |
| C1-H1 ANAc | 1.7-3.0 |
| C1-H1 ANAc-αred | <LC |
| C1-H1 ANS-red | 2.6-5.4 |
| C1-H1 1,6-an.A | <1.1 |
| C1-H1 1,6-an.M | <1.0 |
| C1-H1 MNS-αred | 0.9-2.3 |
| C1-H1 I2S | 30.4-34.9 |
| C1-H1 I-A6S | 1.4-2.6 |
| C1-H1 I-A6OH | <0.2 |
| C1-H1 G-ANS,3S | <2.5 |
| C1-H1 G-ANS | 1.9-3.6 |
| C1-H1 G-ANAc | 0.4-1.4 |
| C1-H1 G2S | <0.5 |
| C1-H1 ΔU2S | 10.9-14.9 |

-continued

| Signal | Relative proportion, % |
|---|---|
| C1-H1 ΔU | 0.6-1.6 |
| C1-H1 I2S-red | <0.5 |
| C5-H5 Gal-A | <0.3 |

Example 5

Study by ¹H NMR of Dalteparin Sodium

The main ¹H chemical shift signals identified were as follows.

| Signal | Chemical shift, ppm |
|---|---|
| H1 ANS(-G) | 5.585 |
| H1 ANS6S | 5.405 |
| H1 I2S | 5.228 |
| H1 I2S-(AM.ol) | 5.178 |
| H1 I | 5.012 |
| H5 I2S | 4.836 |
| H1 G | 4.628 |
| H6 ANS6S | 4.344 |
| H6' ANS6S | 4.210 |
| H3 ANS | 3.670 |
| H2 ANS3S | 3.395 |
| H2 ANS | 3.293 |
| NAc | 2.047 |
| DMMA | 1.320 |
| TSP | 0.069 |

After normalization, correlation and relative content determination, the quantitative relative content (proportion) of each saccharide in dalteparin sodium was obtained and is detailed in the following table. The quantitation (based upon a series of six samples) is based upon the the characteristic and well-differentiated signals of dalteparin sodium (generally those corresponding to the anomeric or target protons, H1).

| Signal | Chemical shift, ppm | Relative proportion, % |
|---|---|---|
| H1 ANS6S | 5.40 | 25.5-25.8 |
| H1 I2S | 5.23 | 19.2-20.8 |
| H1 I2S-(AM.ol) | 5.18 | 9.5-9.8 |
| H2 ANS | 3.29 | 28.0-30.0 |
| NAc | 2.05 | 15.4-20.0 |

Example 6

The same solution used in example 5 was used to perform the study by ¹H-¹³C HSQC. The main ¹H and ¹³C chemical shift signals identified were as follows:

| Signal | δ ¹³C, ppm | δ ¹H, ppm | Signal | δ ¹³C, ppm | δ ¹H, ppm |
|---|---|---|---|---|---|
| C1—H1 G // Gal | 106.62 | 4.66 | C4—H4 ANS6S(-G) | 80.94 | 3.84 |
| C1—H1 Xyl | 105.79 | 4.45 | C2—H2 I2S | 78.53 | 4.34 |
| C1—H1 G(-ANAc) | 105.13 | 4.50 | C3—H3 Xyl | 77.82 | 3.72 |
| C1—H1 I(-A6S) | 104.94 | 5.01 | C2—H2 G(-AN6S) | 75.70 | 3.40 |
| C1—H1 G(-ANS) | 104.77 | 4.60 | C3—H3 ANS6S (-G) | 72.47 | 3.66 |
| C1—H1 I(-A6OH) | 104.67 | 4.94 | C5—H5 I2S | 72.01 | 4.83 |
| C1—H1 G(-ANS3S) | 103.91 | 4.61 | C3—H3 I2S | 71.87 | 4.21 |
| C1—H1 G2S | 102.99 | 4.75 | C5—H5 ANS6S(-G) | 71.72 | 4.09 |
| C1—H1 I2S | 102.09 | 5.22 | C5—H5 Xyl | 65.89 | 4.12 |
| C1—H1 ANS(-G) | 100.50 | 5.58 | C5—H5 Xyl | 65.86 | 3.40 |
| C1—H1 ANAc | 100.23 | 5.31 | C6—H6 Gal | 63.90 | 3.74 |
| C1—H1 ANS(-I2S) | 99.78 | 5.40 | AM.ol-6S | 63.8/63.7 | 3.70/3.74 |
| C1—H1 ANS6S | 99.43 | 5.43 | C2—H2 ANS(-I2S) | 60.82 | 3.28 |
| C1—H1 ANS,3S | 99.06 | 5.51 | C2—H2 ANS6S(-G) | 60.52 | 3.29 |
| C1—H1 ANS(-I) | 98.42 | 5.34 | C2—H2 ANAc | 56.68 | 3.92 |
| C3—H3 Gal | 85.45 | 3.78 | DMMA | 26.73 | 1.32 |
| C3—H3 Gal | 84.85 | 3.83 | NAc | 24.87 | 2.05 |

These signals can be associated with the monosaccharide components of the molecule, so that their quantification allows for the determination of their monosaccharide composition.

The integrals of each one of these signals were normalized starting from the value established for the integral of DMMA, using the same procedure explained for the experiments ¹H NMR. The quantification of the signals characteristic of dalteparin sodium are shown in the following table.

| Signal | Relative proportion, % |
|---|---|
| C1—H1 ANS-I2S | 22.2-23.3 |
| C1—H1 ANS-I | 3.0-3.2 |
| C1—H1 ANS-G | 2.3-2.6 |
| C1—H1 ANS,3S | 2.1-2.9 |
| C1—H1 ANAc | 2.4-3.1 |
| C1—H1 I2S | 24.5-27.5 |
| C1—H1 I-A6S | 3.6-4.0 |
| C1—H1 G-ANS,3S | 1.8-2.3 |
| C1—H1 G-ANS | 2.5-3.5 |
| C1—H1. C6—H6 AM.ol-6S | 20.8-21.7 |

Example 7

Study by ¹H NMR of Tinzaparin Sodium

The main ¹H chemical shift signals identified were as follows:

| Signal | Chemical shift, ppm |
|---|---|
| H4 ΔU2S | 5.992 |
| H4 ΔU | 5.825 |
| H1 ANS(-G) | 5.585 |
| H1 ΔU2S | 5.509 |
| H1 ANS6S | 5.405 |
| H1 I2S | 5.228 |
| H1 I | 5.012 |
| H5 I2S | 4.836 |
| H1 G | 4.628 |
| H6 ANS6S | 4.344 |
| H6' ANS6S | 4.210 |
| H3 ANS | 3.670 |
| H2 ANS3S | 3.395 |
| H2 ANS | 3.293 |
| NAc | 2.047 |
| DMMA | 1.320 |
| TSP | 0.069 |

The quantification of the characteristic and well-differentiated signals of tinzaparin sodium (generally those corresponding to the anomeric or target protons, H1) are shown in the following table, with the values of relative proportions observed (based upon a series of six samples).

| Signal | Chemical shift, ppm | Relative proportion, % |
|---|---|---|
| H4 ΔU2S | 5.99 | 2.7 |
| H1 ΔU2S | 5.51 | 5.3 |
| H1 ANS6S | 5.40 | 23.6 |
| H1 I2S | 5.23 | 21.0 |
| H2 ANS | 3.29 | 30.0 |
| NAc | 2.05 | 16.1 |

Example 8

The same solution used in example 7 was used to perform the study by $^1$H-$^{13}$C HSQC. The main signals identified were as follows:

| Signal | δ $^{13}$C, ppm | δ $^1$H, ppm | Signal | δ $^{13}$C, ppm | δ $^1$H, ppm |
|---|---|---|---|---|---|
| C4—H4 ΔU | 110.71 | 5.82 | C3—H3 Gal | 85.45 | 3.78 |
| C4—H4 ΔU2S | 108.97 | 5.99 | C3—H3 Gal | 84.85 | 3.83 |
| C1—H1 G // Gal | 106.62 | 4.66 | C4—H4 ANS6S(-G) // ANS6S red | 80.94 | 3.84 |
| C1—H1 Xyl | 105.79 | 4.45 | | | |
| C1—H1 G(-ANAc) | 105.13 | 4.50 | C2—H2 I2S | 78.53 | 4.34 |
| C1—H1 I(-A6S) | 104.94 | 5.01 | C3—H3 Xyl | 77.82 | 3.72 |
| C1—H1 G(-ANS) | 104.77 | 4.60 | C2—H2 ΔU2S | 77.42 | 4.62 |
| C1—H1 I(-A6OH) | 104.67 | 4.94 | C2—H2 G(-AN6S) | 75.70 | 3.40 |
| C1—H1 Gal | 104.30 | 4.54 | C3—H3 ANS6S (-G) | 72.47 | 3.66 |
| C1—H1 G(-ANS3S) | 103.91 | 4.61 | C3—H3 ANS6S red | 72.29 | 3.77 |
| C1—H1 ΔU | 103.88 | 5.16 | C5—H5 I2S | 72.01 | 4.83 |
| C1—H1 G2S | 102.99 | 4.75 | C3—H3 I2S | 71.87 | 4.21 |
| C1—H1 I2S | 102.09 | 5.22 | C5—H5 ANS6S(-G) | 71.72 | 4.09 |
| C1—H1 ANS(-G) | 100.50 | 5.58 | C5—H5 ANS6S red | 70.64 | 4.12 |
| C1—H1 ANAc | 100.23 | 5.31 | C5—H5 Xyl | 65.89 | 4.12 |
| C1—H1 ΔU2S | 100.18 | 5.51 | C5—H5 Xyl | 65.86 | 3.40 |
| C1—H1 ANS(-I2S) | 99.78 | 5.40 | C3—H3 ΔU2S | 65.75 | 4.32 |
| C1—H1 ANS6S | 99.43 | 5.43 | C6—H6 Gal | 63.90 | 3.74 |
| C1—H1 ANS,3S | 99.06 | 5.51 | C2—H2 ANS6S red // ANS(-I2S) | 60.82 | 3.28 |
| C1—H1 ANS βred | 98.73 | 4.71 | | | |
| C1—H1 ANS(-I) | 98.42 | 5.34 | C2—H2 ANS6S(-G) | 60.52 | 3.29 |
| C1—H1 I2S αred | 95.70 | 5.42 | C2—H2 MNS6S red | 60.38 | 3.60 |
| C1—H1 I2S βred | 94.76 | 4.97 | C2—H2 ANAc | 56.68 | 3.92 |
| C1—H1 ANS αred // ANS6S red | 93.97 | 5.45 | DMMA | 26.73 | 1.32 |
| | | | NAc | 24.87 | 2.05 |

These signals can be associated with the monosaccharide components of the molecule, so that their quantification allows the determination of their monosaccharide composition.

The integrals of each one of these signals were normalized starting from the value established for the integral of DMMA, using the same procedure explained for the experiments $^1$H RMN. The quantification of the signals characteristic of tinzaparin sodium are shown in the following table:

| Signal | Relative proportion, % |
|---|---|
| C1—H1 ANS-I2S | 27.2 |
| C1—H1 ANS-I | 3.2 |
| C1—H1 ANS-G | 3.4 |
| C1—H1 ANS.3S | 1.2 |
| C1—H1 ANAc | 3.7 |
| C1—H1 ANAc-αred | <LC |
| C1—H1 ANS-red | 6.5 |
| C1—H1 I2S | 35.1 |
| C1—H1 I-A6S | 3.1 |
| C1—H1 I-A6OH | 0.8 |
| C1—H1 G-ANS,3S | 1.5 |
| C1—H1 G-ANS | 3.4 |
| C1—H1 G-ANAc | 2.2 |
| C1—H1 ΔU2S | 8.6 |
| C1—H1 I2S-red | <0.1 |

These experiments show that, using the above-described experimental conditions, it is possible to obtain a method of analysis by nuclear magnetic resonance ($^1$H-RMN y $^1$H-$^{13}$C HSQC) of glycosaminoglycans in general and of heparins and low molecular weight heparins and their derivatives in particular, which allows their quantitative analysis.

Additional Disclosure

The invention includes at least the following embodiments.

A method for the analysis of a composition that contains monosaccharide residues present in heparin chains by means of H-NMR one-dimensional nuclear magnetic resonance and/or $^1$H-$^{13}$C HSQC two-dimensional nuclear magnetic resonance comprising the steps of providing a composition including at least one monosaccharide residue present in heparin chains and obtaining its spectrum of $^1$H-NMR one-dimensional nuclear magnetic resonance and/or $^1$H-$^{13}$C HSQC two-dimensional nuclear magnetic resonance using dimethylmalonic acid (DMMA) as internal reference, and identifying in the NMR spectrum the presence or the absence of at least one signal of at least one residue selected from the group consisting of 4,5-unsaturated 2-O sulfo uronic acid (ΔU2S), 4,5-unsaturated uronic acid (ΔU), 2-N-sulfo-1,6-anhydroglucosamine (1,6-an.A), 2-N-sulfo-1,6-anhydro-mannosamine (1,6-an.M), 2-N-sulfo-6-O-sulfoglucosamine (ANS6S), 2,5-anhydro mannitol, N-sulfoglucosamine, glucuronic acid, N-sulfo-6-O-sulfoglucosamine, 2-O-sulfoiduronic acid, iduronic acid, N-sulfo-3-O-sulfoglucosamine, N-sulfo-3.6-di-O-sulfoglucosamine, galacturonic acid, Xylose, N-acetylglucosamine and N-acetyl-6-O-sulfoglucosamine, characterized in that the presence of said NMR signals in a determined relative proportion of its normalized integrals with respect to DMMA, or the absence thereof, forms a pattern which allows identifying the heparin which the monosaccharide residue comes from comparing the pattern obtained in the analysis with a standard pattern previously obtained for different heparins in the same conditions.

The method according to any of the embodiments herein, wherein the following pattern is identified in the $^1$H NMR spectrum:

| Signal | Chemical shift, ppm | Relative proportion, % |
|---|---|---|
| H4 ΔU2S | 5.99 | 4.3-4.7 |
| H4 ΔU | 5.82 | 0.2 |
| H1 1,6-an.A | 5.62 | 0.7-0.9 |
| H1 1,6-an.M | 5.57 | 4.1-4.4 |
| H1 ΔU2S | 5.51 | 5.7-6.0 |
| H1 ANS6S | 5.40 | 16.1-16.7 |
| H1 I2S | 5.23 | 13.1-14.4 |
| H5 I2S | 4.84 | 14.3-16.3 |
| H2 ANS | 3.29 | 24.3-26.6 |
| NAc | 2.05 | 12.0-15.3 | thereby determining the content of the monosaccharide residues in enoxaparin sodium.

The method according to any of the embodiments herein, wherein the following pattern is identified in the 1H-$^{13}$C HSQC NMR spectrum:

| Signal | Relative proportion, % |
|---|---|
| C1—H1 ANS-I2S | 25.6-26.9 |
| C1—H1 ANS-I | 2.6-3.0 |
| C1—H1 ANS-G | 5.1-5.5 |
| C1—H1 ANS.3S | 1.5-1.7 |
| C1—H1 ANAc | 2.7-3.5 |
| C1—H1 ANAc-αred | <LC |
| C1—H1 ANS-red | 3.8-4.9 |
| C1—H1 1,6-an.A | 1.2-1.5 |
| C1—H1 1,6-an.M | 1.6-1.9 |
| C1—H1 MNS-αred | 1.0-1.3 |
| C1—H1 I2S | 24.5-27.5 |
| C1—H1 I-A6S | 2.4-2.7 |
| C1—H1 I-A6OH | 0.3-0.4 |
| C1—H1 G-ANS.3S | 1.4-1.6 |
| C1—H1 G-ANS | 4.2-4.4 |
| C1—H1 G-ANAc | 1.9-2.6 |
| C1—H1 G2S | 1.1-1.6 |
| C1—H1 ΔU2S | 11.5-12.4 |
| C1—H1 ΔU | 0.3-0.5 |
| C1—H1 I2S-red | 1.0-1.4 |
| C5-H5 Gal-A | <LC-0.5 |
| Epox | <LC-0.4 | where "LC" is "limit of quantification", thereby determining the content of the monosaccharide residues in enoxaparin sodium.

The method according to any of the embodiments herein, wherein the following pattern is identified in the $^1$H NMR spectrum:

| Signal | Chemical shift, ppm | Relative proportion, % |
|---|---|---|
| H4 ΔU2S | 5.99 | 3.7-5.7 |
| H4 ΔU | 5.82 | 0.2-2.5 |
| H1 1,6-an.A | 5.62 | 0.5-2.5 |
| H1 1,6-an.M | 5.57 | 2.5-6.0 |
| H1 ΔU2S | 5.51 | 7.0-10.7 |
| H1 ANS6S | 5.40 | 19.0-21.3 |
| H1 I2S | 5.23 | 13.8-18.5 |
| H2 ANS | 3.29 | 18.7-26.3 |
| NAc | 2.05 | 9.4-14 | thereby determining the content of the monosaccharide residues in bemiparin sodium.

The method according to any of the embodiments herein, wherein the following pattern is identified in the 1H-$^{13}$C HSQC NMR spectrum:

| Signal | Relative proportion, % |
|---|---|
| C1—H1 ANS-I2S | 26.5-30.6 |
| C1—H1 ANS-I | 1.7-5.3 |
| C1—H1 ANS-G | 2.1-3.8 |
| C1—H1 ANS.3S | 0.6-2.5 |
| C1—H1 ANAc | 1.7-3.0 |
| C1—H1 ANAc-αred | <LC |
| C1—H1 ANS-red | 2.6-5.4 |
| C1—H1 1,6-an.A | <1.1 |
| C1—H1 1,6-an.M | <1.0 |
| C1—H1 MNS-αred | 0.9-2.3 |
| C1—H1 I2S | 30.4-34.9 |
| C1—H1 I-A6S | 1.4-2.6 |
| C1—H1 I-A6OH | <0.2 |
| C1—H1 G-ANS,3S | <2.5 |
| C1—H1 G-ANS | 1.9-3.6 |
| C1—H1 G-ANAc | 0.4-1.4 |
| C1—H1 G2S | <0.5 |
| C1—H1 ΔU2S | 10.9-14.9 |
| C1—H1 ΔU | 0.6-1.6 |
| C1—H1 I2S-red | <0.5 |
| C5-H5 Gal-A | <0.3 | thereby determining the content of the monosaccharide residues in bemiparin sodium.

The method according to any of the embodiments herein, wherein the following pattern is identified in the $^1$H NMR spectrum:

| Signal | Chemical shift, ppm | Relative proportion, % |
|---|---|---|
| H1 ANS6S | 5.40 | 25.5-25.8 |
| H1 I2S | 5.23 | 19.2-20.8 |
| H1 I2S-(AM.ol) | 5.18 | 9.5-9.8 |
| H2 ANS | 3.29 | 28.0-30.0 |
| NAc | 2.05 | 15.4-20.0 | thereby determining the content of the monosaccharide residues in dalteparin sodium.

The method according to any of the embodiments herein, wherein the following pattern is identified in the 1H-$^{13}$C HSQC NMR spectrum:

| Signal | Relative proportion, % |
|---|---|
| C1—H1 ANS-I2S | 22.2-23.3 |
| C1—H1 ANS-I | 3.0-3.2 |
| C1—H1 ANS-G | 2.3-2.6 |
| C1—H1 ANS,3S | 2.1-2.9 |
| C1—H1 ANAc | 2.4-3.1 |
| C1—H1 I2S | 24.5-27.5 |
| C1—H1 I-A6S | 3.6-4.0 |
| C1—H1 G-ANS,3S | 1.8-2.3 |
| C1—H1 G-ANS | 2.5-3.5 |
| C1—H1. C6-H6 AM.ol-6S | 20.8-21.7 | thereby determining the content of the monosaccharide residues in dalteparin sodium.

The method according to any of the embodiments herein, wherein the following pattern is identified in the $^1$H NMR spectrum:

| Signal | Chemical shift, ppm | Relative proportion, % |
|---|---|---|
| H4 ΔU2S | 5.99 | 2.7 |
| H1 ΔU2S | 5.51 | 5.3 |
| H1 ANS6S | 5.40 | 23.6 |
| H1 I2S | 5.23 | 21.0 |
| H2 ANS | 3.29 | 30.0 |
| NAc | 2.05 | 16.1 | thereby determining the content of the monosaccharide residues in tinzaparin sodium.

The method according to any of the embodiments herein, wherein the following pattern is identified in the 1H-$^{13}$C HSQC NMR spectrum:

| Signal | Relative proportion, % |
|---|---|
| C1—H1 ANS-I2S | 27.2 |
| C1—H1 ANS-I | 3.2 |
| C1—H1 ANS-G | 3.4 |
| C1—H1 ANS,3S | 1.2 |
| C1—H1 ANAc | 3.7 |
| C1—H1 ANAc-αred | <LC |
| C1—H1 ANS-red | 6.5 |
| C1—H1 I2S | 35.1 |
| C1—H1 I-A6S | 3.1 |
| C1—H1 I-A6OH | 0.8 |
| C1—H1 G-ANS,3S | 1.5 |
| C1—H1 G-ANS | 3.4 |
| C1—H1 G-ANAc | 2.2 |
| C1—H1 ΔU2S | 8.6 |
| C1—H1 I2S-red | <0.1 | thereby determining the content of the monosaccharide residues in tinzaparin sodium.

The method according to any of the embodiments herein, wherein the signals corresponding to the N-acetyl groups appear in the region between 1.8 to 2.1 ppm in of $^1$H-NMR spectroscopy.

The method according to any of the embodiments herein, wherein the signals corresponding to the saccharide ring of said residues appear in the region between 2.8 to 6.0 ppm in $^1$H-NMR spectroscopy.

The method according to any of the embodiments herein, wherein the signals corresponding to the anomeric or target H1 protons, and that of the H4 protons of the non-reducing ends of one of said residues, appear in the region between 4.5 to 6.0 ppm in $^1$H-NMR spectroscopy.

The method according to any of the embodiments herein, wherein, in $^1$H NMR spectroscopy, the 4,5-unsaturated 2-O-sulfo-uronic acid (ΔU2S) signals appear at 5.99 and 5.51 ppm, for the H4 and anomeric protons respectively, the 4,5-unsaturated uronic acid (ΔU) signal appears at 5.82 ppm for the H4 proton, the 2-N-sulfo-1,6-anhydroglucosamine (1,6-an.A) signal appears at 5.62 ppm for the anomeric proton, the 2-N-sulfo-1,6-anhydro-mannosamine (1,6-an.M) signal appears at 5.57 ppm for the anomeric proton, and the 2-N-sulfo-6-O-sulfoglucosamine signals appear at 5.41 and 4.21-4.34 ppm for the H1 and H6 and H6' protons respectively.

The method according to any of the embodiments herein, wherein, in 1H-$^{13}$C HSQC NMR spectroscopy, the 4,5-unsaturated 2-O sulfo uronic acid (ΔU2S) signals appear at 6.0-109.0 ppm (H4-C4), 5.5-100.2 ppm (H1-C1), 4.6-77.4 ppm (H2-C2) or 4.3-66.8 ppm (H3-C3), the 4,5-unsaturated uronic acid (ΔU) signals appear at 5.8-110.7 ppm (H4-C4) or 5.2-103.9 ppm (H1-C1), the 2-N-sulfo-1,6-anhydroglucosamine (1,6-an.A) signals appear at 5.6-104.2 ppm (H1-C1), 3.2-58.5 ppm (H2-C2) or 3.8-67.5 ppm (H6-C6), the 2-N-sulfo-1,6-anhydro-mannosamine (1,6-an.M) signals appear at 5.6-103.9 ppm (H1-C1), 3.5-55.1 (H2-C2) or 3.8-67.5 ppm (H6-C6), and the 2-N-sulfo-6-O-sulfoglucosamine signals appear at 5.4-99.4 ppm (H1-C1), 3.8-80.9 ppm (H4-C4), 3.7 to 3.8-42.3 to 72.5 ppm (H3-C3), 4.1-70.6 to 71.7 ppm (H5-C5) or 3.3-60.5-60.8 ppm (H2-C2).

The method according to any of the embodiments herein, wherein the pattern obtained in the analysis is such that it determines that the monosaccharide residues come from an unfractionated heparin.

The method according to any of the embodiments herein, wherein the pattern obtained in the analysis is such that it determines that the monosaccharide residues come from a Low Molecular Weight Heparin (LMWH).

The method according to any of the embodiments herein, wherein the pattern obtained in the analysis is such that it determines that the monosaccharide residues come from an Ultra Low Molecular Weight Heparin (ULMWH).

The invention according to any of the embodiments herein, wherein the glycosaminoglycan is selected from the group consisting of enoxaparin, bemiparin, dalteparin, tinzaparin, a salt of any of the preceding, a derivative of any of the preceding, or a combination thereof.

In view of the above description and the examples below, one of ordinary skill in the art will be able to practice the invention as claimed without undue experimentation. The foregoing will be better understood with reference to the following examples that detail certain procedures for the preparation and/or practice of embodiments of the present invention. All references made to these examples are for the purposes of illustration. The following examples should not be considered exhaustive, but merely illustrative of only a few of the many embodiments contemplated by the present invention.

As used herein, the term "about" or "approximately" are taken to mean ±10%, ±5%, ±2.5% or ±1% of a specified valued. As used herein, the term "substantially" is taken to mean "to a large degree" or "at least a majority of" or "more than 50% of". Moreover, all ranges specified herein are inclusive of the range limits and all integer and fractional values therein especially as defined by the definition of the term "about".

As used herein a "derivative" is: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosylated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

The invention claimed is:

1. A nuclear magnetic resonance (NMR) method for identifying and/or quantifying the content of one or more individual saccharides in one or more glycosaminoglycans in a composition, the method comprising at least the step of:
   providing a composition comprising: i) at least one glycosaminoglycan (GAG) comprising plural saccharides comprising respective anomeric or target hydrogen atoms exhibiting respective anomeric or target $^1$H chemical shift signals when analyzed by NMR; and ii) at least one reference compound comprising a hydrogen atom having a NMR signal T1 longitudinal relaxation time of 1 s or less, wherein the at least one reference compound exhibits a reference $^1$H NMR chemical shift signal separated from said anomeric or target $^1$H chemical shift signals, and said reference $^1$H chemical shift signal exhibits a concentration dependent intensity;
   conducting at least one NMR analysis, on said composition, selected from the group consisting of one-dimensional (1D)$^1$H-NMR analysis, two-dimensional (2D) H-$^{13}$C-NMR analysis, or a combination of said analyses, to provide at least one GAG NMR spectrum;
   thereby providing the content of said one or more individual saccharides and/or providing the identity of said one or more individual saccharides.

2. The method of claim 1 further comprising comparing the intensities of said anomeric or target $^1$H chemical shift signals to the intensity of the reference $^1$H chemical shift signal.

3. The method of claim 1 further comprising obtaining the integrals for said anomeric or target $^1$H chemical shift signals and said reference $^1$H chemical shift signal.

4. The method of claim 3 further comprising dividing said integrals for said anomeric or target $^1$H chemical shift signals by the integral of said reference $^1$H chemical shift signal to provide normalized values of said integrals for said anomeric or target $^1$H chemical shift signals.

5. The method of claim 4 further comprising determining the relative proportions of said anomeric or target hydrogens with respect to the total amount of anomeric or target hydrogens present in said glycosaminoglycan to provide the content of saccharide in said one or more glycosaminoglycans.

6. The method of claim 5 further comprising correlating the relative proportions of said anomeric or target hydrogens with the relative proportions of corresponding saccharides present in said glycosaminoglycan.

7. The method of claim 1 further comprising a providing a reference $^1$H NMR spectrum for each of said plural saccharides being quantified, b) providing a reference $^1$H-NMR spectrum for said at least one glycosaminoglycan; and/or c) determining the relative proportions of anomeric or target hydrogens in one or more reference glycosaminoglycans.

8. The method of claim 7 further comprising correlating said relative proportions of anomeric or target hydrogens with the relative proportions of corresponding saccharides present in said one or more reference glycosaminoglycans.

9. The method of claim 1 further comprising:
   a) developing a calibration curve for said at least one glycosaminoglycan; b) developing a calibration curve for said at least one reference compound; c) developing calibration curves for said plural saccharides; or d) a combination of any two or more of the above.

10. The method of claim 1 further a) comprising providing a standard defining 0 ppm; or b) using the singlet $^1$H-NMR or $^{13}$C-NMR chemical shift of 3-(trimethylsilyl)-priopionic-D4 acid as a chemical shift reference for 0 ppm.

11. The method of claim 1, wherein said concentration dependent intensity is substantially linear in the range of about 0.2 mM to about 2.5 mM of said at least one reference compound.

12. The method of claim 1 further comprising providing at least one deuterated solvent i-s selected from the group consisting of D$_2$O, any solvent that will solubilize the at least one GAG and the at least one reference compound, and a combination of D$_2$O and said any solvent.

13. The method of claim 1, wherein a) said at least one reference compound is present at a concentration in the range of about 0.2 mM to about 2.5 mM, b) said at least one reference compound is present at a known or predetermined concentration or amount; and/or c) said at least one reference compound is dimethylmalonic acid (DMMA).

14. The method of claim 1, wherein a) said at least one glycosaminoglycan is present at a known or predetermined concentration or amount or at a concentration in the range of about 0.02 to about 0.2 mg/μL, b) said glycosaminoglycan is an oligosaccharide or polysaccharide; c) said at least one glycosaminoglycan is selected from the group consisting of heparin, heparan, enoxaparin, bemiparin, dalteparin, tinzaparin, a salt of any of the preceding, a derivative of any of the preceding, a sulfated non-sulfated form of any of the preceding, an ultra-low molecular weight form of an of the preceding, a low molecular weight form of an of the preceding, a high molecular weight form of an of the preceding, an unfractionated form of any of the preceding, a fractionated form of an of the preceding, and a combination of any thereof and/or d) said at least one saccharide is selected from the group consisting of 4,5-unsaturated 2-O sulfo-uronic acid (ΔU2S), 4,5-unsaturated uronic acid (ΔU) 2-N-sulfo-1,6-anhydroglucosamine (1,6-an.A) 2-N-sulfo-1,6-anhydro-mannosamine (16-an.M), 2-N-sulfo-6-O-sulfoglucosamine (ANS6S), 2,5-anhydro mannitol, N-sulfoglucosamine, glucuronic acid, N-sulfo-6-O-sulfoglucosamine, 2-O-sulfoiduronic acid, iduronic acid, N-sulfo-3-O-sulfoglucosamine, N-sulfo-3,6-di-O-sulfoglucosamine, galacturonic acid, Xylose, N-acetylglucosamine and N-acetyl-6-O-sulfoglucosamine.

15. A nuclear magnetic resonance (NMR) method for identifying and/or quantifying the content of one or more individual saccharides in one or more glycosaminoglycans in a composition, the method comprising at least the step of:
   providing a composition comprising: i) at least one glycosaminoglycan (GAG) comprising plural saccharides comprising respective anomeric or target hydrogen atoms exhibiting respective anomeric or target $^1$H chemical shift signals when analyzed by NMR and further comprising respective anomeric or target carbon atoms covalently bound to said anomeric or target hydrogens atoms and exhibiting respective anomeric or target $^{13}$C chemical shift signals when analyzed by NMR; and ii) at least one reference compound comprising a hydrogen atom having a NMR signal tI longitudinal relaxation time of 1 s or less and a respective carbon atom covalently bound to said hydrogen atom, wherein said at least one reference compound exhibits a reference $^1$H NMR chemical shift signal separated from said anomeric or target $^1$H chemical shift signals and further exhibits a reference $^{13}$C NMR chemical shift signal separated from said anomeric or target $^{13}$C chemical shift signals, and said reference $^1$H chemical shift signal and said reference $^{13}$C chemical shift signal each exhibits a concentration dependent intensity;

conducting at least one NMR analysis, on said composition, selected from the group consisting of one-dimensional (1D)$^{13}$C-NMR analysis, two-dimensional (2D) $^1$H-$^{13}$C-NMR analysis, or a combination of said analyses, to provide at least one GAG NMR spectrum;

thereby providing the content of said one or more individual saccharides and/or providing the identity of said one or more individual saccharides.

16. The method of claim 15 further comprising comparing the intensities of said anomeric or target $^{13}$C chemical shift signals to the intensity of the reference $^{13}$C chemical shift signal.

17. The method of claim 15 further comprising: a) obtaining the integrals for said anomeric or target $^1$H chemical shift signals and said reference $^1$H chemical shift signal; b) obtaining the integrals for said anomeric or target $^{13}$C chemical shift signals and said reference $^{13}$C chemical shift signal; or c) a combination of a) and b).

18. The method of claim 17 further comprising: a) dividing said integrals for said anomeric or target $^1$H chemical shift signals by the integral of said reference $^1$H chemical shift signal to provide normalized values of said integrals for said anomeric or target $^1$H chemical shift signals; b) dividing said integrals for said anomeric or target $^{13}$C chemical shift signals by the integral of said reference $^{13}$C chemical shift signal to provide normalized values of said integrals for said anomeric or target $^{13}$C chemical shift signals; or c) a combination of a) and b).

19. The method of claim 18 further comprising: a) determining the relative proportions of said anomeric or target hydrogens with respect to the total amount of anomeric or target hydrogens present in said glycosaminoglycan to provide the content of saccharide in said one or more glycosaminoglycans; b) determining the relative proportions of said anomeric or target carbons with respect to the total amount of anomeric or target carbons present in said glycosaminoglycan to provide the content of saccharide in said one or more glycosaminoglycans; or c) a combination of a) or b).

20. The method of claim 19 further comprising: a) correlating the relative proportions of said anomeric or target hydrogens with the relative proportions of corresponding saccharides present in said glycosaminoglycan; b) correlating the relative proportions of said anomeric or target carbons with the relative proportions of corresponding saccharides present in said glycosaminoglycan; or c) a combination of a) or b).

21. The method of claim 15 further comprising a) providing a reference $^1$H NMR spectrum and/or reference $^{13}$C NMR spectrum for each of said plural saccharides being quantified, and/or b) providing a reference $^{13}$C-NMR spectrum for said at least one glycosaminoglycan.

22. The method of claim 21 further comprising: a) determining the relative proportions of anomeric or target hydrogens in one or more reference glycosaminoglycans; b) determining the relative proportions of anomeric or target carbons in one or more reference glycosaminoglycans; or c) a combination of a) or b).

23. The method of claim 22 further comprising: a) correlating said relative proportions of anomeric or target hydrogens with the relative proportions of corresponding saccharides present in said one or more reference glycosaminoglycans; b) correlating said relative proportions of anomeric or target carbons with the relative proportions of corresponding saccharides present in said one or more reference glycosaminoglycans; or c) a combination of a) or b).

24. The method of claim 15, wherein a) said at least one NMR analysis comprises exposing said composition to plural magnetic pulses such that the time between individual magnetic pulses (d1) is about 1 s to about 2 s, b) said respective anomeric or target $^{13}$C chemical shift signal in the range of about 55 ppm to about 115 ppm; c) said reference $^{13}$C NMR chemical shift signal is n the range of about 25-27 ppm; d) said respective anomeric or target $^1$H chemical s si n the range of about 32 ppm about 6 ppm; e) said reference $^1$H-NMR chemical shift signal is a singlet within the range of about 1.2 ppm to about 1.6 ppm inclusive of the range limits.

25. A method for identifying and/or quantifying the content of one or more individual saccharides in one or more glycosaminoglycans in a composition, the method comprising at least:

providing said composition comprising at least a) one or more glycosaminoglycan comprising one or more individual saccharides comprising anomeric or target hydrogen exhibiting respective anomeric or target $^1$H chemical shift signal in the range of about 3.2 ppm to about 6 ppm when analyzed by NMR; b) dimethylmalonic acid as reference compound comprising a hydrogen atom having a NMR signal T1 longitudinal relaxation time of 1 s or less, wherein said reference compound exhibits a reference $^1$H NMR chemical shift signal separated from said anomeric or target $^1$H chemical shift signals, and said reference $^1$H chemical shift signal exhibits a concentration dependent intensity; and c) chemical shift reference standard defining 0 ppm;

conducting at least one NMR analysis, on said composition, selected from the group consisting of one-dimensional (1D)$^1$H-NMR analysis, two-dimensional (2D) H-$^{13}$C-NMR analysis, or a combination of said analyses, to provide at least one GAG NMR spectrum; and comparing the intensities of said anomeric or target $^1$H chemical shift signals to the intensity of the reference $^1$H chemical shift signal;

thereby providing the content of and/or providing the identity of said one or more individual saccharides in said one or more glycosaminoglycans.

26. The method of claim 25 further comprising obtaining the integrals for said anomeric or target $^1$H chemical shift signals and said reference $^1$H chemical shift signal.

27. The method of claim 26 further comprising dividing said integrals for said anomeric or target $^1$H chemical shift signals by the integral of said reference $^1$H chemical shift signal to provide normalized values of said integrals for said anomeric or target $^1$H chemical shift signals.

28. The method of claim 27 further comprising determining the relative proportions of said anomeric or target hydrogens with respect to the total amount of anomeric or target hydrogens present in said glycosaminoglycan to provide the content of saccharide in said one or more glycosaminoglycans.

29. The method of claim 28 further comprising correlating the relative proportions of said anomeric or target hydrogens with the relative proportions of corresponding saccharides present in said glycosaminoglycan.

30. The method of claim 25 further comprising determining the relative proportions of anomeric or target hydrogens in one or more reference glycosaminoglycans.

31. The method of claim 30 further comprising correlating said relative proportions of anomeric or target hydrogens with the relative proportions of corresponding saccharides present in said one or more reference glycosaminoglycans.

* * * * *

UNITED STATES PATENT AND TRADEMARK OFFICE
CERTIFICATE OF CORRECTION

PATENT NO.         : 10,809,212 B2
APPLICATION NO.    : 16/824895
DATED              : October 20, 2020
INVENTOR(S)        : Guillermo Franco Rodriguez and Ibon Gutierro Aduriz It is certified that error appears in the above-identified patent and that said Letters Patent is hereby corrected as shown below:

In the Claims

Column 38, Lines 24-28 of Claim 12: correct text to read as follows:
12. The method of claim 1 further comprising providing at least one deuterated solvent selected from the group consisting of $D_2O$, any solvent that will solubilize the at least GAG and the at least one reference compound, and a combination of $D_2O$ and said any solvent.

Column 39, Lines 6-7 of Claim 15: correct text to read as follows:
NMR: and ii) at least one reference compound comprising a hydrogen atom having a NMR signal T1

Column 40, Lines 26-28 of Claim 24: correct text to read as follows:
$^{13}$CNMR chemical shift signal is in the range of about 25-27 ppm; d) said respective anomeric or target $^1$H chemical shift signal is in the range of about 3.2 ppm to about 6 ppm; e) said reference Signed and Sealed this
Nineteenth Day of January, 2021

Andrei Iancu
*Director of the United States Patent and Trademark Office*